(12) United States Patent
Mayse et al.

(10) Patent No.: US 12,343,060 B2
(45) Date of Patent: *Jul. 1, 2025

(54) NON-INVASIVE AND MINIMALLY INVASIVE DENERVATION METHODS AND SYSTEMS FOR PERFORMING THE SAME

(71) Applicant: Nuvaira, Inc., Minneapolis, MN (US)

(72) Inventors: Martin L. Mayse, Wayzata, MN (US); Steven C. Dimmer, Bellevue, WA (US)

(73) Assignee: Nuvaira, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/362,591

(22) Filed: Jul. 31, 2023

(65) Prior Publication Data
US 2024/0090936 A1 Mar. 21, 2024

Related U.S. Application Data

(63) Continuation of application No. 16/842,062, filed on Apr. 7, 2020, now Pat. No. 11,712,283, which is a
(Continued)

(51) Int. Cl.
*A61B 18/08* (2006.01)
*A61B 17/00* (2006.01)
(Continued)

(52) U.S. Cl.
CPC ...... *A61B 18/082* (2013.01); *A61B 17/00234* (2013.01); *A61B 18/04* (2013.01);
(Continued)

(58) Field of Classification Search
CPC ... A61B 17/00234; A61B 18/02; A61B 18/04; A61B 18/082; A61B 18/1477;
(Continued)

(56) References Cited

U.S. PATENT DOCUMENTS 612,724 A 10/1898 Hamilton
1,155,169 A 9/1915 John
(Continued)

FOREIGN PATENT DOCUMENTS

CA 2419228 A1 8/2004
CN 101115448 A 1/2008
(Continued)

OTHER PUBLICATIONS

Abbott., "Present Concepts Relative to Autonomic Nerve Surgery in the Treatment of Pulmonary Disease," American Journal of Surgery, 1955, vol. 90, pp. 479-489.
(Continued)

*Primary Examiner* — Khadijeh A Vahdat
(74) *Attorney, Agent, or Firm* — Husch Blackwell LLP

(57) ABSTRACT

A system and method can be used to denervate at least a portion of a bronchial tree. An energy emitter of an instrument is percutaneously delivered to a treatment site and outputs energy to damage nerve tissue of the bronchial tree. The denervation procedure can be performed without damaging non-targeted tissue. Minimally invasive methods can be used to open airways to improve lung function in subjects with COPD, asthma, or the like. Different sections of the bronchial tree can be denervated while leaving airways intact to reduce recovery times.

20 Claims, 9 Drawing Sheets

Related U.S. Application Data continuation of application No. 15/596,192, filed on May 16, 2017, now Pat. No. 10,610,283, which is a continuation of application No. 14/541,931, filed on Nov. 14, 2014, now Pat. No. 9,649,154, which is a continuation of application No. 12/944,666, filed on Nov. 11, 2010, now Pat. No. 8,911,439.

(60) Provisional application No. 61/260,350, filed on Nov. 11, 2009.

(51) Int. Cl.
| | |
|---|---|
| *A61B 18/04* | (2006.01) |
| *A61B 18/14* | (2006.01) |
| *A61B 18/18* | (2006.01) |
| *A61N 5/06* | (2006.01) |
| *A61N 5/10* | (2006.01) |
| *A61N 7/00* | (2006.01) |
| *A61N 7/02* | (2006.01) |
| *A61B 18/00* | (2006.01) |
| *A61B 18/02* | (2006.01) |

(52) U.S. Cl.
CPC .......... *A61B 18/1492* (2013.01); *A61B 18/18* (2013.01); *A61B 18/1815* (2013.01); *A61N 5/0601* (2013.01); *A61N 5/062* (2013.01); *A61N 5/1077* (2013.01); *A61N 7/00* (2013.01); *A61N 7/022* (2013.01); *A61B 2017/00323* (2013.01); *A61B 2018/0022* (2013.01); *A61B 2018/00279* (2013.01); *A61B 2018/00291* (2013.01); *A61B 2018/00434* (2013.01); *A61B 2018/00541* (2013.01); *A61B 2018/00577* (2013.01); *A61B 2018/00642* (2013.01); *A61B 2018/00982* (2013.01); *A61B 18/02* (2013.01); *A61B 2018/0212* (2013.01); *A61B 2018/1425* (2013.01); *A61B 18/1477* (2013.01); *A61B 2018/1861* (2013.01); *A61N 2005/0604* (2013.01); *A61N 2005/0651* (2013.01); *A61N 2007/003* (2013.01)

(58) Field of Classification Search
CPC . A61B 18/1492; A61B 18/18; A61B 18/1815; A61B 2017/00323; A61B 2018/0022; A61B 2018/00279; A61B 2018/00291; A61B 2018/00434; A61B 2018/00541; A61B 2018/00577; A61B 2018/00642; A61B 2018/00982; A61B 2018/0212; A61B 2018/1425; A61B 2018/1861
See application file for complete search history.

(56) References Cited

U.S. PATENT DOCUMENTS

| | | |
|---|---|---|
| 1,207,479 A | 12/1916 | Holger |
| 1,216,183 A | 2/1917 | Swingle |
| 1,695,107 A | 12/1928 | Kahl |
| 2,072,346 A | 3/1937 | Smith |
| 2,279,714 A | 4/1942 | Meyerhof et al. |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,918,449 A | 11/1975 | Pistor |
| 3,946,745 A | 3/1976 | Hsiang-Lai et al. |
| 3,949,743 A | 4/1976 | Shanbrom |
| 3,995,617 A | 12/1976 | Watkins et al. |
| 4,078,864 A | 3/1978 | Howell |
| 4,095,602 A | 6/1978 | Leveen |
| 4,116,589 A | 9/1978 | Rishton |
| 4,129,129 A | 12/1978 | Amrine |
| 4,154,246 A | 5/1979 | LeVeen |
| 4,277,168 A | 7/1981 | Oku |
| 4,305,402 A | 12/1981 | Katims |
| 4,351,330 A | 9/1982 | Scarberry |
| 4,461,283 A | 7/1984 | Doi |
| 4,502,490 A | 3/1985 | Evans et al. |
| 4,503,855 A | 3/1985 | Maslanka |
| 4,503,863 A | 3/1985 | Katims |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,573,481 A | 3/1986 | Bullara |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,649,924 A | 3/1987 | Taccardi |
| 4,649,935 A | 3/1987 | Charmillot et al. |
| 4,658,836 A | 4/1987 | Turner |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,322 A | 8/1988 | Charmillot et al. |
| 4,765,959 A | 8/1988 | Fukasawa |
| 4,767,402 A | 8/1988 | Kost et al. |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,808,164 A | 2/1989 | Hess |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,881,542 A | 11/1989 | Schmidt et al. |
| 4,895,557 A | 1/1990 | Moise et al. |
| 4,902,129 A | 2/1990 | Siegmund et al. |
| 4,904,472 A | 2/1990 | Belardinelli et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,945,910 A | 8/1990 | Budyko et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,989,604 A | 2/1991 | Fang |
| 4,991,603 A | 2/1991 | Cohen et al. |
| 4,992,474 A | 2/1991 | Skidmore et al. |
| 5,005,559 A | 4/1991 | Blanco et al. |
| 5,007,908 A | 4/1991 | Rydell |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,054,486 A | 10/1991 | Yamada |
| 5,056,519 A | 10/1991 | Vince |
| 5,056,529 A | 10/1991 | De Groot |

(56) References Cited

U.S. PATENT DOCUMENTS

| | | |
|---|---|---|
| 5,057,107 A | 10/1991 | Parins et al. |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,107,835 A | 4/1992 | Thomas |
| 5,109,846 A | 5/1992 | Thomas |
| 5,114,423 A | 5/1992 | Kasprzyk et al. |
| 5,116,864 A | 5/1992 | March et al. |
| 5,117,828 A | 6/1992 | Metzger et al. |
| 5,123,413 A | 6/1992 | Hasegawa et al. |
| 5,126,375 A | 6/1992 | Skidmore et al. |
| 5,135,480 A | 8/1992 | Bannon et al. |
| 5,135,517 A | 8/1992 | McCoy |
| 5,139,029 A | 8/1992 | Fishman et al. |
| 5,151,100 A | 9/1992 | Abele et al. |
| 5,152,286 A | 10/1992 | Sitko et al. |
| 5,165,420 A | 11/1992 | Strickland |
| 5,167,223 A | 12/1992 | Koros et al. |
| 5,170,802 A | 12/1992 | Mehra |
| 5,170,803 A | 12/1992 | Hewson et al. |
| 5,174,288 A | 12/1992 | Bardy et al. |
| 5,188,602 A | 2/1993 | Nichols |
| 5,190,540 A | 3/1993 | Lee |
| 5,191,883 A | 3/1993 | Lennox et al. |
| 5,213,576 A | 5/1993 | Abiuso et al. |
| 5,215,103 A | 6/1993 | Desai |
| 5,224,491 A | 7/1993 | Mehra |
| 5,225,445 A | 7/1993 | Skidmore et al. |
| 5,231,996 A | 8/1993 | Bardy et al. |
| 5,232,444 A | 8/1993 | Just et al. |
| 5,234,456 A | 8/1993 | Silvestrini |
| 5,239,982 A | 8/1993 | Trauthen |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,286,254 A | 2/1994 | Shapland et al. |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,255 A | 6/1994 | Passafaro et al. |
| 5,324,284 A | 6/1994 | Imran |
| 5,343,936 A | 9/1994 | Beatenbough et al. |
| 5,344,398 A | 9/1994 | Hara |
| 5,345,936 A | 9/1994 | Pomeranz et al. |
| 5,348,554 A | 9/1994 | Imran et al. |
| 5,366,443 A | 11/1994 | Eggers et al. |
| 5,368,591 A | 11/1994 | Lennox et al. |
| 5,370,644 A | 12/1994 | Langberg |
| 5,370,675 A | 12/1994 | Edwards et al. |
| 5,370,679 A | 12/1994 | Atlee, III |
| 5,372,603 A | 12/1994 | Acker et al. |
| 5,374,287 A | 12/1994 | Rubin |
| 5,379,765 A | 1/1995 | Kajiwara et al. |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,405,362 A | 4/1995 | Kramer et al. |
| 5,405,366 A | 4/1995 | Fox et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,454,840 A | 10/1995 | Krakovsky et al. |
| 5,456,667 A | 10/1995 | Ham et al. |
| 5,458,596 A | 10/1995 | Lax et al. |
| 5,465,717 A | 11/1995 | Imran et al. |
| 5,470,352 A | 11/1995 | Rappaport |
| 5,471,982 A | 12/1995 | Edwards et al. |
| 5,474,530 A | 12/1995 | Passafaro et al. |
| 5,478,309 A | 12/1995 | Sweezer et al. |
| 5,478,578 A | 12/1995 | Arnold et al. |
| 5,496,271 A | 3/1996 | Burton et al. |
| 5,496,304 A | 3/1996 | Chasan |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'Ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,540,730 A | 7/1996 | Terry, Jr. et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,553,611 A | 9/1996 | Budd et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,620,463 A | 4/1997 | Drolet |
| 5,623,940 A | 4/1997 | Daikuzono |
| 5,624,392 A | 4/1997 | Saab |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,630,813 A | 5/1997 | Kieturakis |
| 5,634,471 A | 6/1997 | Fairfax et al. |
| 5,641,326 A | 6/1997 | Adams |
| 5,647,870 A | 7/1997 | Kordis et al. |
| 5,658,278 A | 8/1997 | Imran et al. |
| 5,658,322 A | 8/1997 | Fleming |
| 5,658,549 A | 8/1997 | Akehurst et al. |
| 5,660,175 A | 8/1997 | Dayal |
| 5,662,108 A | 9/1997 | Budd et al. |
| 5,669,930 A | 9/1997 | Igarashi |
| 5,669,932 A | 9/1997 | Fischell et al. |
| 5,674,472 A | 10/1997 | Akehurst et al. |

(56) References Cited

U.S. PATENT DOCUMENTS

| | | |
|---|---|---|
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,690,692 A | 11/1997 | Fleming |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,707,400 A | 1/1998 | Terry, Jr. et al. |
| 5,722,401 A | 3/1998 | Pietroski et al. |
| 5,722,403 A | 3/1998 | Mcgee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,733,319 A | 3/1998 | Neilson et al. |
| 5,735,846 A | 4/1998 | Panescu et al. |
| 5,740,808 A | 4/1998 | Panescu et al. |
| 5,741,248 A | 4/1998 | Stern et al. |
| 5,746,224 A | 5/1998 | Edwards |
| 5,752,518 A | 5/1998 | Mcgee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,766,605 A | 6/1998 | Sanders et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,800,486 A | 9/1998 | Thome et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,814,078 A | 9/1998 | Zhou et al. |
| 5,817,028 A | 10/1998 | Anderson |
| 5,817,073 A | 10/1998 | Krespi |
| 5,820,554 A | 10/1998 | Davis et al. |
| 5,820,589 A | 10/1998 | Torgerson et al. |
| 5,823,189 A | 10/1998 | Kordis |
| 5,827,277 A | 10/1998 | Edwards |
| 5,833,651 A | 11/1998 | Donovan et al. |
| 5,836,874 A | 11/1998 | Swanson et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,843,088 A | 12/1998 | Barra et al. |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,483 A | 2/1999 | Jackson et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,027 A | 4/1999 | Tu et al. |
| 5,891,135 A | 4/1999 | Jackson et al. |
| 5,891,136 A | 4/1999 | Mcgee et al. |
| 5,891,138 A | 4/1999 | Tu et al. |
| 5,891,182 A | 4/1999 | Fleming |
| 5,893,847 A | 4/1999 | Kordis |
| 5,893,887 A | 4/1999 | Jayaraman |
| 5,897,554 A | 4/1999 | Chia et al. |
| 5,899,882 A | 5/1999 | Waksman et al. |
| 5,902,268 A | 5/1999 | Saab |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,806 A | 8/1999 | Shimada |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,956,501 A | 9/1999 | Brown |
| 5,957,919 A | 9/1999 | Laufer |
| 5,957,961 A | 9/1999 | Maguire et al. |
| 5,964,223 A | 10/1999 | Baran |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,989,545 A | 11/1999 | Foster et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,995,873 A | 11/1999 | Rhodes |
| 5,997,534 A | 12/1999 | Tu et al. |
| 5,999,855 A | 12/1999 | DiMarco |
| 6,001,054 A | 12/1999 | Regula et al. |
| 6,003,517 A | 12/1999 | Sheffield et al. |
| 6,004,269 A | 12/1999 | Crowley et al. |
| 6,006,134 A | 12/1999 | Hill et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |

(56) References Cited

U.S. PATENT DOCUMENTS

| | | |
|---|---|---|
| 6,039,731 A | 3/2000 | Taylor et al. |
| 6,043,273 A | 3/2000 | Duhaylongsod |
| 6,045,549 A | 4/2000 | Smethers et al. |
| 6,045,550 A | 4/2000 | Simpson et al. |
| 6,050,992 A | 4/2000 | Nichols |
| 6,052,607 A | 4/2000 | Edwards et al. |
| 6,053,172 A | 4/2000 | Hovda et al. |
| 6,053,909 A | 4/2000 | Shadduck |
| 6,056,744 A | 5/2000 | Edwards |
| 6,056,745 A | 5/2000 | Panescu et al. |
| 6,056,769 A | 5/2000 | Epstein et al. |
| 6,060,454 A | 5/2000 | Duhaylongsod |
| 6,063,078 A | 5/2000 | Wittkampf |
| 6,063,768 A | 5/2000 | First |
| 6,071,280 A | 6/2000 | Edwards et al. |
| 6,071,281 A | 6/2000 | Burnside et al. |
| 6,071,282 A | 6/2000 | Fleischman |
| 6,081,749 A | 6/2000 | Ingle et al. |
| 6,083,249 A | 7/2000 | Familoni |
| 6,083,255 A | 7/2000 | Laufer et al. |
| 6,087,394 A | 7/2000 | Duhaylongsod |
| 6,090,104 A | 7/2000 | Webster, Jr. |
| 6,091,995 A | 7/2000 | Ingle et al. |
| 6,092,528 A | 7/2000 | Edwards |
| 6,097,985 A | 8/2000 | Kasevich et al. |
| 6,101,412 A | 8/2000 | Duhaylongsod |
| 6,102,886 A | 8/2000 | Lundquist et al. |
| 6,106,524 A | 8/2000 | Eggers et al. |
| 6,117,101 A | 9/2000 | Diederich et al. |
| 6,123,702 A | 9/2000 | Swanson et al. |
| 6,123,703 A | 9/2000 | Tu et al. |
| 6,123,718 A | 9/2000 | Tu et al. |
| 6,125,301 A | 9/2000 | Capel |
| 6,127,410 A | 10/2000 | Duhaylongsod |
| 6,129,726 A | 10/2000 | Edwards et al. |
| 6,135,997 A | 10/2000 | Laufer et al. |
| 6,139,527 A | 10/2000 | Laufer et al. |
| 6,139,571 A | 10/2000 | Fuller et al. |
| 6,139,845 A | 10/2000 | Donovan |
| 6,141,589 A | 10/2000 | Duhaylongsod |
| 6,142,993 A | 11/2000 | Whayne et al. |
| 6,143,013 A | 11/2000 | Samson et al. |
| 6,143,277 A | 11/2000 | Ashurst et al. |
| 6,149,647 A | 11/2000 | Tu et al. |
| 6,152,143 A | 11/2000 | Edwards |
| 6,152,899 A | 11/2000 | Farley et al. |
| 6,152,953 A | 11/2000 | Hipskind |
| 6,159,194 A | 12/2000 | Eggers et al. |
| 6,163,716 A | 12/2000 | Edwards et al. |
| 6,174,323 B1 | 1/2001 | Biggs et al. |
| 6,179,833 B1 | 1/2001 | Taylor |
| 6,183,468 B1 | 2/2001 | Swanson et al. |
| 6,197,013 B1 | 3/2001 | Reed et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,203,562 B1 | 3/2001 | Ohkubo |
| 6,210,367 B1 | 4/2001 | Carr |
| 6,212,432 B1 | 4/2001 | Matsuura |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,216,704 B1 | 4/2001 | Ingle et al. |
| 6,217,576 B1 | 4/2001 | Tu et al. |
| 6,226,543 B1 | 5/2001 | Gilboa et al. |
| 6,230,052 B1 | 5/2001 | Wolff et al. |
| 6,231,595 B1 | 5/2001 | Dobak, III |
| 6,235,024 B1 | 5/2001 | Tu |
| 6,240,307 B1 | 5/2001 | Beatty et al. |
| 6,241,727 B1 | 6/2001 | Tu et al. |
| 6,245,065 B1 | 6/2001 | Panescu et al. |
| 6,251,368 B1 | 6/2001 | Akehurst et al. |
| 6,253,762 B1 | 7/2001 | Britto |
| 6,254,598 B1 | 7/2001 | Edwards et al. |
| 6,254,599 B1 | 7/2001 | Lesh et al. |
| 6,258,083 B1 | 7/2001 | Daniel et al. |
| 6,258,087 B1 | 7/2001 | Edwards et al. |
| 6,264,653 B1 | 7/2001 | Falwell |
| 6,265,379 B1 | 7/2001 | Donovan |
| 6,269,813 B1 | 8/2001 | Fitzgerald et al. |
| 6,270,476 B1 | 8/2001 | Santoianni et al. |
| 6,273,886 B1 | 8/2001 | Edwards et al. |
| 6,273,907 B1 | 8/2001 | Laufer |
| 6,283,987 B1 | 9/2001 | Laird et al. |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,302,870 B1 | 10/2001 | Jacobsen et al. |
| 6,303,509 B1 | 10/2001 | Chen et al. |
| 6,306,423 B1 | 10/2001 | Donovan et al. |
| 6,315,173 B1 | 11/2001 | Di Giovanni et al. |
| 6,315,778 B1 | 11/2001 | Gambale et al. |
| 6,317,615 B1 | 11/2001 | Kenknight et al. |
| 6,322,559 B1 | 11/2001 | Daulton et al. |
| 6,322,584 B2 | 11/2001 | Ingle et al. |
| 6,325,798 B1 | 12/2001 | Edwards et al. |
| 6,327,503 B1 | 12/2001 | Familoni |
| 6,338,727 B1 | 1/2002 | Noda et al. |
| 6,338,836 B1 | 1/2002 | Kuth et al. |
| 6,341,236 B1 | 1/2002 | Osorio et al. |
| 6,346,104 B2 | 2/2002 | Daly et al. |
| 6,355,031 B1 | 3/2002 | Edwards et al. |
| 6,356,786 B1 | 3/2002 | Rezai et al. |
| 6,356,787 B1 | 3/2002 | Rezai et al. |
| 6,357,447 B1 | 3/2002 | Swanson et al. |
| 6,358,245 B1 | 3/2002 | Edwards et al. |
| 6,358,926 B2 | 3/2002 | Donovan |
| 6,361,554 B1 | 3/2002 | Brisken |
| 6,363,937 B1 | 4/2002 | Hovda et al. |
| 6,366,814 B1 | 4/2002 | Boveja et al. |
| 6,379,352 B1 | 4/2002 | Reynolds et al. |
| 6,383,509 B1 | 5/2002 | Donovan et al. |
| 6,394,956 B1 | 5/2002 | Chandrasekaran et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,411,852 B1 | 6/2002 | Danek et al. |
| 6,414,018 B1 | 7/2002 | Duhaylongsod |
| 6,416,511 B1 | 7/2002 | Lesh et al. |
| 6,416,740 B1 | 7/2002 | Unger |
| 6,423,058 B1 | 7/2002 | Edwards et al. |
| 6,423,105 B1 | 7/2002 | Iijima et al. |
| 6,424,864 B1 | 7/2002 | Matsuura |
| 6,425,877 B1 | 7/2002 | Edwards |
| 6,425,887 B1 | 7/2002 | McGuckin et al. |
| 6,425,895 B1 | 7/2002 | Swanson et al. |
| 6,432,092 B2 | 8/2002 | Miller |
| 6,436,130 B1 | 8/2002 | Philips et al. |
| 6,438,423 B1 | 8/2002 | Rezai et al. |
| 6,440,128 B1 | 8/2002 | Edwards et al. |
| 6,440,129 B1 | 8/2002 | Simpson |
| 6,442,435 B2 | 8/2002 | King et al. |
| 6,447,505 B2 | 9/2002 | Mcgovern et al. |
| 6,447,785 B1 | 9/2002 | Donovan |
| 6,448,231 B2 | 9/2002 | Graham |
| 6,458,121 B1 | 10/2002 | Rosenstock et al. |
| 6,460,545 B2 | 10/2002 | Kordis |
| 6,464,680 B1 | 10/2002 | Brisken et al. |
| 6,464,697 B1 | 10/2002 | Edwards et al. |
| 6,475,160 B1 | 11/2002 | Sher |
| 6,480,746 B1 | 11/2002 | Ingle et al. |
| 6,485,416 B1 | 11/2002 | Platt et al. |
| 6,488,673 B1 | 12/2002 | Laufer et al. |
| 6,488,679 B1 | 12/2002 | Swanson et al. |
| 6,491,710 B2 | 12/2002 | Satake |
| 6,493,589 B1 | 12/2002 | Medhkour et al. |
| 6,494,880 B1 | 12/2002 | Swanson et al. |
| 6,496,737 B2 | 12/2002 | Rudie et al. |
| 6,496,738 B2 | 12/2002 | Carr |
| 6,506,399 B2 | 1/2003 | Donovan |

(56) References Cited

U.S. PATENT DOCUMENTS

| | | |
|---|---|---|
| 6,510,969 B2 | 1/2003 | Di Giovanni et al. |
| 6,514,246 B1 | 2/2003 | Swanson et al. |
| 6,514,290 B1 | 2/2003 | Loomas |
| 6,519,488 B2 | 2/2003 | Kenknight et al. |
| 6,522,913 B2 | 2/2003 | Swanson et al. |
| 6,524,555 B1 | 2/2003 | Ashurst et al. |
| 6,526,320 B2 | 2/2003 | Mitchell |
| 6,526,976 B1 | 3/2003 | Baran |
| 6,529,756 B1 | 3/2003 | Phan et al. |
| 6,532,388 B1 | 3/2003 | Hill et al. |
| 6,533,780 B1 | 3/2003 | Laird et al. |
| 6,536,427 B2 | 3/2003 | Davies et al. |
| 6,544,226 B1 | 4/2003 | Gaiser et al. |
| 6,544,262 B2 | 4/2003 | Fleischman |
| 6,546,928 B1 | 4/2003 | Ashurst et al. |
| 6,546,932 B1 | 4/2003 | Nahon et al. |
| 6,546,934 B1 | 4/2003 | Ingle et al. |
| 6,547,776 B1 | 4/2003 | Gaiser et al. |
| 6,547,788 B1 | 4/2003 | Maguire et al. |
| 6,549,808 B1 | 4/2003 | Gisel et al. |
| 6,551,274 B2 | 4/2003 | Heiner |
| 6,551,310 B1 | 4/2003 | Ganz et al. |
| 6,558,333 B2 | 5/2003 | Gilboa et al. |
| 6,558,378 B2 | 5/2003 | Sherman et al. |
| 6,558,381 B2 | 5/2003 | Ingle et al. |
| 6,562,034 B2 | 5/2003 | Edwards et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,587,718 B2 | 7/2003 | Talpade |
| 6,587,719 B1 | 7/2003 | Barrett et al. |
| 6,587,731 B1 | 7/2003 | Ingle et al. |
| 6,589,235 B2 | 7/2003 | Wong et al. |
| 6,589,238 B2 | 7/2003 | Edwards et al. |
| 6,593,130 B1 | 7/2003 | Sen et al. |
| 6,599,311 B1 | 7/2003 | Biggs et al. |
| 6,601,581 B1 | 8/2003 | Babaev |
| 6,603,996 B1 | 8/2003 | Beatty et al. |
| 6,610,054 B1 | 8/2003 | Edwards et al. |
| 6,610,083 B2 | 8/2003 | Keller et al. |
| 6,610,713 B2 | 8/2003 | Tracey |
| 6,613,002 B1 | 9/2003 | Clark et al. |
| 6,613,045 B1 | 9/2003 | Laufer et al. |
| 6,620,159 B2 | 9/2003 | Hegde |
| 6,620,415 B2 | 9/2003 | Donovan |
| 6,622,047 B2 | 9/2003 | Barrett et al. |
| 6,623,742 B2 | 9/2003 | Voet |
| 6,626,855 B1 | 9/2003 | Weng et al. |
| 6,626,903 B2 | 9/2003 | McGuckin, Jr. et al. |
| 6,629,535 B2 | 10/2003 | Ingle et al. |
| 6,629,951 B2 | 10/2003 | Laufer et al. |
| 6,632,440 B1 | 10/2003 | Quinn et al. |
| 6,633,779 B1 | 10/2003 | Schuler et al. |
| 6,634,363 B1 | 10/2003 | Danek et al. |
| 6,635,054 B2 | 10/2003 | Fjield et al. |
| 6,635,056 B2 | 10/2003 | Kadhiresan et al. |
| 6,638,273 B1 | 10/2003 | Farley et al. |
| 6,640,119 B1 | 10/2003 | Budd et al. |
| 6,640,120 B1 | 10/2003 | Swanson et al. |
| 6,645,200 B1 | 11/2003 | Koblish et al. |
| 6,645,496 B2 | 11/2003 | Aoki et al. |
| 6,647,617 B1 | 11/2003 | Beatty et al. |
| 6,648,881 B2 | 11/2003 | Kenknight et al. |
| 6,649,161 B1 | 11/2003 | Donovan |
| 6,652,517 B1 | 11/2003 | Hall et al. |
| 6,652,548 B2 | 11/2003 | Evans et al. |
| 6,656,960 B2 | 12/2003 | Puskas |
| 6,658,279 B2 | 12/2003 | Swanson et al. |
| 6,663,622 B1 | 12/2003 | Foley et al. |
| 6,666,858 B2 | 12/2003 | Lafontaine |
| 6,669,693 B2 | 12/2003 | Friedman |
| 6,673,068 B1 | 1/2004 | Berube |
| 6,673,070 B2 | 1/2004 | Edwards et al. |
| 6,675,047 B1 | 1/2004 | Konoplev et al. |
| 6,676,686 B2 | 1/2004 | Naganuma |
| 6,681,136 B2 | 1/2004 | Schuler et al. |
| 6,692,492 B2 | 2/2004 | Simpson et al. |
| 6,692,494 B1 | 2/2004 | Cooper et al. |
| 6,699,180 B2 | 3/2004 | Kobayashi |
| 6,699,243 B2 | 3/2004 | West et al. |
| 6,708,064 B2 | 3/2004 | Rezai |
| 6,711,436 B1 | 3/2004 | Duhaylongsod |
| 6,712,074 B2 | 3/2004 | Edwards et al. |
| 6,712,812 B2 | 3/2004 | Roschak et al. |
| 6,712,814 B2 | 3/2004 | Edwards et al. |
| 6,714,822 B2 | 3/2004 | King et al. |
| 6,719,685 B2 | 4/2004 | Fujikura et al. |
| 6,719,694 B2 | 4/2004 | Weng et al. |
| 6,723,053 B2 | 4/2004 | Ackerman et al. |
| 6,723,091 B2 | 4/2004 | Goble et al. |
| 6,728,562 B1 | 4/2004 | Budd et al. |
| 6,735,471 B2 | 5/2004 | Hill et al. |
| 6,735,475 B1 | 5/2004 | Whitehurst et al. |
| 6,740,321 B1 | 5/2004 | Donovan |
| 6,743,197 B1 | 6/2004 | Edwards |
| 6,743,413 B1 | 6/2004 | Schultz et al. |
| 6,749,604 B1 | 6/2004 | Eggers et al. |
| 6,749,606 B2 | 6/2004 | Keast et al. |
| 6,752,765 B1 | 6/2004 | Jensen et al. |
| 6,755,026 B2 | 6/2004 | Wallach |
| 6,755,849 B1 | 6/2004 | Gowda et al. |
| 6,767,347 B2 | 7/2004 | Sharkey et al. |
| 6,767,544 B2 | 7/2004 | Brooks et al. |
| 6,770,070 B1 | 8/2004 | Balbierz |
| 6,772,013 B1 | 8/2004 | Ingle et al. |
| 6,773,711 B2 | 8/2004 | Voet et al. |
| 6,776,991 B2 | 8/2004 | Naumann |
| 6,777,423 B2 | 8/2004 | Banholzer et al. |
| 6,778,854 B2 | 8/2004 | Puskas |
| 6,780,183 B2 | 8/2004 | Jimenez, Jr. et al. |
| 6,786,889 B1 | 9/2004 | Musbach et al. |
| 6,802,843 B2 | 10/2004 | Truckai et al. |
| 6,805,131 B2 | 10/2004 | Kordis |
| 6,819,956 B2 | 11/2004 | DiLorenzo |
| 6,826,420 B1 | 11/2004 | Beatty et al. |
| 6,826,421 B1 | 11/2004 | Beatty et al. |
| 6,827,931 B1 | 12/2004 | Donovan |
| 6,836,688 B2 | 12/2004 | Ingle et al. |
| 6,837,888 B2 | 1/2005 | Ciarrocca et al. |
| 6,838,429 B2 | 1/2005 | Paslin |
| 6,838,434 B2 | 1/2005 | Voet |
| 6,838,471 B2 | 1/2005 | Tracey |
| 6,840,243 B2 | 1/2005 | Deem et al. |
| 6,841,156 B2 | 1/2005 | Aoki et al. |
| 6,843,998 B1 | 1/2005 | Steward et al. |
| 6,846,312 B2 | 1/2005 | Edwards et al. |
| 6,847,849 B2 | 1/2005 | Mamo et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,861,058 B2 | 3/2005 | Aoki et al. |
| 6,866,662 B2 | 3/2005 | Fuimaono et al. |
| 6,871,092 B2 | 3/2005 | Piccone |
| 6,872,206 B2 | 3/2005 | Edwards et al. |
| 6,872,397 B2 | 3/2005 | Aoki et al. |
| 6,878,156 B1 | 4/2005 | Noda |
| 6,881,213 B2 | 4/2005 | Ryan et al. |
| 6,885,888 B2 | 4/2005 | Rezai |
| 6,890,347 B2 | 5/2005 | Machold et al. |
| 6,893,436 B2 | 5/2005 | Woodard et al. |
| 6,893,438 B2 | 5/2005 | Hall et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,908,462 B2 | 6/2005 | Joye et al. |
| 6,908,928 B2 | 6/2005 | Banholzer et al. |
| 6,913,616 B2 | 7/2005 | Hamilton et al. |
| 6,917,834 B2 | 7/2005 | Koblish et al. |
| 6,934,583 B2 | 8/2005 | Weinberg et al. |
| 6,937,896 B1 | 8/2005 | Kroll |
| 6,937,903 B2 | 8/2005 | Schuler et al. |
| 6,939,309 B1 | 9/2005 | Beatty et al. |

(56) References Cited

U.S. PATENT DOCUMENTS

| | | |
|---|---|---|
| 6,939,345 B2 | 9/2005 | Kenknight et al. |
| 6,939,346 B2 | 9/2005 | Kannenberg et al. |
| 6,947,785 B1 | 9/2005 | Beatty et al. |
| 6,954,977 B2 | 10/2005 | Maguire et al. |
| 6,957,106 B2 | 10/2005 | Schuler et al. |
| 6,961,622 B2 | 11/2005 | Gilbert |
| 6,970,742 B2 | 11/2005 | Mann et al. |
| RE38,912 E | 12/2005 | Walz et al. |
| 6,971,395 B2 | 12/2005 | Edwards et al. |
| 6,974,224 B2 | 12/2005 | Thomas-Benedict |
| 6,974,456 B2 | 12/2005 | Edwards et al. |
| 6,974,578 B1 | 12/2005 | Aoki et al. |
| 6,978,168 B2 | 12/2005 | Beatty et al. |
| 6,978,174 B2 | 12/2005 | Gelfand et al. |
| 6,990,370 B1 | 1/2006 | Beatty et al. |
| 6,994,706 B2 | 2/2006 | Chornenky et al. |
| 6,997,189 B2 | 2/2006 | Biggs et al. |
| 7,004,942 B2 | 2/2006 | Laird et al. |
| 7,022,088 B2 | 4/2006 | Keast et al. |
| 7,022,105 B1 | 4/2006 | Edwards |
| 7,027,869 B2 | 4/2006 | Danek et al. |
| 7,043,307 B1 | 5/2006 | Zelickson et al. |
| 7,070,800 B2 | 7/2006 | Bechtold-Peters et al. |
| 7,072,720 B2 | 7/2006 | Puskas |
| 7,083,614 B2 | 8/2006 | Fjield et al. |
| 7,101,368 B2 | 9/2006 | Lafontaine |
| 7,101,387 B2 | 9/2006 | Garabedian et al. |
| 7,104,987 B2 | 9/2006 | Biggs et al. |
| 7,104,990 B2 | 9/2006 | Jenkins et al. |
| 7,112,198 B2 | 9/2006 | Satake |
| 7,118,568 B2 | 10/2006 | Hassett et al. |
| 7,122,031 B2 | 10/2006 | Edwards et al. |
| 7,122,033 B2 | 10/2006 | Wood |
| 7,125,407 B2 | 10/2006 | Edwards et al. |
| 7,131,445 B2 | 11/2006 | Amoah |
| 7,142,910 B2 | 11/2006 | Puskas |
| 7,150,745 B2 | 12/2006 | Stern et al. |
| 7,162,303 B2 | 1/2007 | Levin et al. |
| 7,165,551 B2 | 1/2007 | Edwards et al. |
| 7,167,757 B2 | 1/2007 | Ingle et al. |
| 7,175,644 B2 | 2/2007 | Cooper et al. |
| 7,179,257 B2 | 2/2007 | West et al. |
| 7,186,251 B2 | 3/2007 | Malecki et al. |
| 7,187,964 B2 | 3/2007 | Khoury |
| 7,187,973 B2 | 3/2007 | Hauck |
| 7,189,208 B1 | 3/2007 | Beatty et al. |
| 7,198,635 B2 | 4/2007 | Danek et al. |
| 7,200,445 B1 | 4/2007 | Dalbec et al. |
| 7,229,469 B1 | 6/2007 | Witzel et al. |
| 7,238,357 B2 | 7/2007 | Barron |
| 7,241,295 B2 | 7/2007 | Maguire |
| 7,255,693 B1 | 8/2007 | Johnston et al. |
| RE39,820 E | 9/2007 | Banholzer et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,289,843 B2 | 10/2007 | Beatty et al. |
| 7,291,146 B2 | 11/2007 | Steinke et al. |
| 7,292,890 B2 | 11/2007 | Whitehurst et al. |
| 7,309,707 B2 | 12/2007 | Bender et al. |
| 7,310,552 B2 | 12/2007 | Puskas |
| RE40,045 E | 2/2008 | Palmer |
| 7,326,207 B2 | 2/2008 | Edwards |
| 7,344,535 B2 | 3/2008 | Stern et al. |
| 7,371,231 B2 | 5/2008 | Rioux et al. |
| 7,393,330 B2 | 7/2008 | Keast et al. |
| 7,393,350 B2 | 7/2008 | Maurice |
| 7,394,976 B2 | 7/2008 | Entenman et al. |
| 7,402,172 B2 | 7/2008 | Chin et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,430,449 B2 | 9/2008 | Aldrich et al. |
| 7,462,162 B2 | 12/2008 | Phan et al. |
| 7,462,179 B2 | 12/2008 | Edwards et al. |
| 7,473,273 B2 | 1/2009 | Campbell |
| 7,477,945 B2 | 1/2009 | Rezai et al. |
| 7,483,755 B2 | 1/2009 | Ingle et al. |
| 7,493,160 B2 | 2/2009 | Weber et al. |
| 7,494,661 B2 | 2/2009 | Sanders |
| 7,507,234 B2 | 3/2009 | Utley et al. |
| 7,507,238 B2 | 3/2009 | Edwards et al. |
| 7,517,320 B2 | 4/2009 | Wibowo et al. |
| 7,530,979 B2 | 5/2009 | Ganz et al. |
| 7,532,938 B2 | 5/2009 | Machado et al. |
| 7,542,802 B2 | 6/2009 | Danek et al. |
| 7,553,307 B2 | 6/2009 | Bleich et al. |
| 7,556,624 B2 | 7/2009 | Laufer et al. |
| 7,559,890 B2 | 7/2009 | Wallace et al. |
| 7,572,245 B2 | 8/2009 | Herweck et al. |
| 7,585,296 B2 | 9/2009 | Edwards et al. |
| 7,588,549 B2 | 9/2009 | Eccleston |
| 7,594,925 B2 | 9/2009 | Danek et al. |
| 7,608,275 B2 | 10/2009 | Deem et al. |
| 7,613,515 B2 | 11/2009 | Knudson et al. |
| 7,617,005 B2 | 11/2009 | Demarais et al. |
| 7,620,451 B2 | 11/2009 | Demarais et al. |
| 7,628,789 B2 | 12/2009 | Soltesz et al. |
| 7,632,268 B2 | 12/2009 | Edwards et al. |
| 7,641,632 B2 | 1/2010 | Noda et al. |
| 7,641,633 B2 | 1/2010 | Laufer et al. |
| 7,648,500 B2 | 1/2010 | Edwards et al. |
| 7,653,438 B2 | 1/2010 | Deem et al. |
| 7,684,865 B2 | 3/2010 | Aldrich et al. |
| 7,689,290 B2 | 3/2010 | Ingle et al. |
| 7,691,079 B2 | 4/2010 | Gobel et al. |
| RE41,334 E | 5/2010 | Beatty et al. |
| 7,708,712 B2 | 5/2010 | Phan et al. |
| 7,708,768 B2 | 5/2010 | Danek et al. |
| 7,711,430 B2 | 5/2010 | Errico et al. |
| 7,717,948 B2 | 5/2010 | Demarais et al. |
| 7,722,538 B2 | 5/2010 | Khoury |
| 7,725,188 B2 | 5/2010 | Errico et al. |
| 7,734,355 B2 | 6/2010 | Cohen et al. |
| 7,734,535 B1 | 6/2010 | Burns |
| 7,740,017 B2 | 6/2010 | Danek et al. |
| 7,740,631 B2 | 6/2010 | Bleich et al. |
| 7,742,795 B2 | 6/2010 | Stone et al. |
| 7,747,324 B2 | 6/2010 | Errico et al. |
| 7,756,583 B2 | 7/2010 | Demarais et al. |
| 7,765,010 B2 | 7/2010 | Chornenky et al. |
| 7,770,584 B2 | 8/2010 | Danek et al. |
| 7,783,358 B2 | 8/2010 | Aldrich et al. |
| 7,815,590 B2 | 10/2010 | Cooper |
| 7,826,881 B1 | 11/2010 | Beatty et al. |
| 7,831,288 B1 | 11/2010 | Beatty et al. |
| 7,837,676 B2 | 11/2010 | Sinelnikov et al. |
| 7,837,679 B2 | 11/2010 | Biggs et al. |
| 7,841,986 B2 | 11/2010 | He et al. |
| 7,844,338 B2 | 11/2010 | Knudson et al. |
| 7,853,331 B2 | 12/2010 | Kaplan et al. |
| 7,854,734 B2 | 12/2010 | Biggs et al. |
| 7,854,740 B2 | 12/2010 | Carney |
| 7,869,879 B2 | 1/2011 | Errico et al. |
| 7,869,880 B2 | 1/2011 | Errico et al. |
| 7,873,417 B2 | 1/2011 | Demarais et al. |
| 7,877,146 B2 | 1/2011 | Rezai et al. |
| 7,904,159 B2 | 3/2011 | Errico et al. |
| 7,906,124 B2 | 3/2011 | Laufer et al. |
| 7,914,448 B2 | 3/2011 | Bob et al. |
| 7,921,855 B2 | 4/2011 | Danek et al. |
| 7,930,012 B2 | 4/2011 | Beatty et al. |
| 7,931,647 B2 | 4/2011 | Wizeman et al. |
| 7,937,143 B2 | 5/2011 | Demarais et al. |
| 7,938,123 B2 | 5/2011 | Danek et al. |
| 7,949,407 B2 | 5/2011 | Kaplan et al. |
| 7,967,782 B2 | 6/2011 | Laufer et al. |
| 7,985,187 B2 | 7/2011 | Wibowo et al. |
| 7,992,572 B2 | 8/2011 | Danek et al. |
| 7,993,336 B2 | 8/2011 | Jackson et al. |
| 8,002,740 B2 | 8/2011 | Willink et al. |
| 8,010,197 B2 | 8/2011 | Errico et al. |
| 8,012,149 B2 | 9/2011 | Jackson et al. |
| 8,041,428 B2 | 10/2011 | Errico et al. |

(56) References Cited

U.S. PATENT DOCUMENTS

| | | |
|---|---|---|
| 8,046,085 B2 | 10/2011 | Knudson et al. |
| 8,052,668 B2 | 11/2011 | Sih |
| 8,088,127 B2 | 1/2012 | Mayse et al. |
| 8,099,167 B1 | 1/2012 | Errico et al. |
| 8,105,817 B2 | 1/2012 | Deem et al. |
| 8,128,595 B2 | 3/2012 | Walker et al. |
| 8,128,617 B2 | 3/2012 | Bencini et al. |
| 8,131,371 B2 | 3/2012 | Demarais et al. |
| 8,133,497 B2 | 3/2012 | Deem et al. |
| 8,152,803 B2 | 4/2012 | Edwards et al. |
| 8,172,827 B2 | 5/2012 | Deem et al. |
| 8,204,598 B2 | 6/2012 | Errico et al. |
| 8,208,998 B2 | 6/2012 | Beatty et al. |
| 8,209,034 B2 | 6/2012 | Simon et al. |
| 8,216,216 B2 | 7/2012 | Warnking et al. |
| 8,226,638 B2 | 7/2012 | Mayse et al. |
| 8,229,564 B2 | 7/2012 | Rezai |
| 8,231,621 B2 | 7/2012 | Hutchins et al. |
| 8,233,988 B2 | 7/2012 | Errico et al. |
| 8,251,992 B2 | 8/2012 | Utley et al. |
| 8,267,094 B2 | 9/2012 | Danek et al. |
| 8,295,902 B2 | 10/2012 | Salahieh et al. |
| 8,303,581 B2 | 11/2012 | Arts et al. |
| 8,313,484 B2 | 11/2012 | Edwards et al. |
| 8,328,798 B2 | 12/2012 | Witzel et al. |
| 8,338,164 B2 | 12/2012 | Deem et al. |
| 8,347,891 B2 | 1/2013 | Demarais et al. |
| 8,357,118 B2 | 1/2013 | Orr |
| 8,364,237 B2 | 1/2013 | Stone et al. |
| 8,371,303 B2 | 2/2013 | Schaner et al. |
| 8,377,055 B2 | 2/2013 | Jackson et al. |
| 8,483,831 B1 | 7/2013 | Hlavka et al. |
| 8,489,192 B1 | 7/2013 | Hlavka et al. |
| 8,660,647 B2 | 2/2014 | Parnis et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,391 B2 | 2/2015 | Deem et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlvaka et al. |
| 9,149,328 B2 | 10/2015 | Dimmer et al. |
| 9,339,618 B2 | 5/2016 | Deem et al. |
| 9,398,933 B2 | 7/2016 | Mayse |
| 9,498,283 B2 | 11/2016 | Deem et al. |
| 9,539,048 B2 | 1/2017 | Hlvaka et al. |
| 9,649,153 B2 | 5/2017 | Mayse et al. |
| 9,649,154 B2 | 5/2017 | Mayse et al. |
| 9,662,171 B2 | 5/2017 | Dimmer et al. |
| 9,668,809 B2 | 6/2017 | Mayse et al. |
| 9,675,412 B2 | 6/2017 | Mayse et al. |
| 9,867,986 B2 | 1/2018 | Hlvaka et al. |
| 9,931,162 B2 | 4/2018 | Mayse et al. |
| 10,022,529 B2 | 7/2018 | Deem et al. |
| 10,149,714 B2 | 12/2018 | Mayse et al. |
| 10,201,386 B2 | 2/2019 | Mayse et al. |
| 10,206,735 B2 | 2/2019 | Kaveckis et al. |
| 10,252,057 B2 | 4/2019 | Hlvaka et al. |
| 10,363,091 B2 | 7/2019 | Dimmer et al. |
| 10,368,937 B2 | 8/2019 | Kaveckis et al. |
| 10,575,893 B2 | 3/2020 | Mayse |
| 10,610,283 B2 | 4/2020 | Mayse et al. |
| 10,729,897 B2 | 8/2020 | Deem et al. |
| 10,869,997 B2 | 12/2020 | Mayse |
| 2001/0020151 A1 | 9/2001 | Reed et al. |
| 2001/0044596 A1 | 11/2001 | Jaafar |
| 2002/0002387 A1 | 1/2002 | Naganuma |
| 2002/0010495 A1 | 1/2002 | Freed et al. |
| 2002/0016344 A1 | 2/2002 | Tracey |
| 2002/0042564 A1 | 4/2002 | Cooper et al. |
| 2002/0042565 A1 | 4/2002 | Cooper et al. |
| 2002/0049370 A1 | 4/2002 | Laufer et al. |
| 2002/0072738 A1 | 6/2002 | Edwards et al. |
| 2002/0082197 A1 | 6/2002 | Aoki et al. |
| 2002/0087153 A1 | 7/2002 | Roschak et al. |
| 2002/0087208 A1 | 7/2002 | Koblish et al. |
| 2002/0091379 A1 | 7/2002 | Danek et al. |
| 2002/0107512 A1 | 8/2002 | Edwards |
| 2002/0107515 A1 | 8/2002 | Edwards et al. |
| 2002/0111386 A1 | 8/2002 | Sekins et al. |
| 2002/0111619 A1 | 8/2002 | Keast et al. |
| 2002/0111620 A1 | 8/2002 | Cooper et al. |
| 2002/0115991 A1 | 8/2002 | Edwards |
| 2002/0116030 A1 | 8/2002 | Rezai |
| 2002/0143302 A1 | 10/2002 | Hinchliffe et al. |
| 2002/0143326 A1 | 10/2002 | Foley et al. |
| 2002/0143373 A1 | 10/2002 | Courtnage et al. |
| 2002/0151888 A1 | 10/2002 | Edwards et al. |
| 2002/0183682 A1 | 12/2002 | Darvish |
| 2002/0198512 A1 | 12/2002 | Seward |
| 2002/0198570 A1 | 12/2002 | Puskas |
| 2002/0198574 A1 | 12/2002 | Gumpert |
| 2003/0018327 A1 | 1/2003 | Truckai et al. |
| 2003/0018344 A1 | 1/2003 | Kaji et al. |
| 2003/0023287 A1 | 1/2003 | Edwards et al. |
| 2003/0027752 A1 | 2/2003 | Steward et al. |
| 2003/0050591 A1 | 3/2003 | Patrick McHale |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0070676 A1 | 4/2003 | Cooper et al. |
| 2003/0074039 A1 | 4/2003 | Puskas |
| 2003/0093069 A1 | 5/2003 | Panescu et al. |
| 2003/0093128 A1 | 5/2003 | Freed et al. |
| 2003/0125786 A1 | 7/2003 | Gliner et al. |
| 2003/0130571 A1 | 7/2003 | Lattouf |
| 2003/0130657 A1 | 7/2003 | Tom et al. |
| 2003/0144572 A1 | 7/2003 | Oschman et al. |
| 2003/0153905 A1 | 8/2003 | Edwards et al. |
| 2003/0159700 A1 | 8/2003 | Laufer et al. |
| 2003/0181949 A1 | 9/2003 | Whale |
| 2003/0187430 A1 | 10/2003 | Vorisek |
| 2003/0195593 A1 | 10/2003 | Ingle et al. |
| 2003/0195604 A1 | 10/2003 | Ingle et al. |
| 2003/0202990 A1 | 10/2003 | Donovan et al. |
| 2003/0208103 A1 | 11/2003 | Sonnenschein et al. |
| 2003/0211121 A1 | 11/2003 | Donovan |
| 2003/0216791 A1 | 11/2003 | Schuler et al. |
| 2003/0216792 A1 | 11/2003 | Levin et al. |
| 2003/0216891 A1 | 11/2003 | Wegener |
| 2003/0225443 A1 | 12/2003 | Kiran et al. |
| 2003/0233099 A1 | 12/2003 | Danaek et al. |
| 2003/0236455 A1 | 12/2003 | Swanson et al. |
| 2004/0006268 A1 | 1/2004 | Gilboa et al. |
| 2004/0009180 A1 | 1/2004 | Donovan |
| 2004/0010289 A1 | 1/2004 | Biggs et al. |
| 2004/0010290 A1 | 1/2004 | Schroeppel et al. |
| 2004/0028676 A1 | 2/2004 | Klein et al. |
| 2004/0029849 A1 | 2/2004 | Schatzberg et al. |
| 2004/0030368 A1 | 2/2004 | Kemeny et al. |
| 2004/0031494 A1 | 2/2004 | Danek et al. |
| 2004/0044390 A1 | 3/2004 | Szeles |
| 2004/0059383 A1 | 3/2004 | Puskas |
| 2004/0073201 A1 | 4/2004 | Cooper et al. |
| 2004/0073206 A1 | 4/2004 | Foley et al. |
| 2004/0073278 A1 | 4/2004 | Pachys |
| 2004/0086531 A1 | 5/2004 | Barron |
| 2004/0087936 A1 | 5/2004 | Stern et al. |
| 2004/0088030 A1 | 5/2004 | Jung, Jr. |
| 2004/0088036 A1 | 5/2004 | Gilbert |
| 2004/0091880 A1 | 5/2004 | Wiebusch et al. |
| 2004/0106954 A1 | 6/2004 | Whitehurst et al. |
| 2004/0116981 A1 | 6/2004 | Mazar |
| 2004/0122488 A1 | 6/2004 | Mazar et al. |
| 2004/0122489 A1 | 6/2004 | Mazar et al. |
| 2004/0127942 A1 | 7/2004 | Yomtov et al. |
| 2004/0127958 A1 | 7/2004 | Mazar et al. |
| 2004/0142005 A1 | 7/2004 | Brooks et al. |

(56) References Cited

U.S. PATENT DOCUMENTS

| | | |
|---|---|---|
| 2004/0147921 A1 | 7/2004 | Edwards et al. |
| 2004/0147969 A1 | 7/2004 | Mann et al. |
| 2004/0147988 A1 | 7/2004 | Stephens |
| 2004/0151741 A1 | 8/2004 | Borodic |
| 2004/0153056 A1 | 8/2004 | Muller et al. |
| 2004/0162584 A1 | 8/2004 | Hill et al. |
| 2004/0162597 A1 | 8/2004 | Hamilton et al. |
| 2004/0167509 A1 | 8/2004 | Taimisto |
| 2004/0167580 A1 | 8/2004 | Mann et al. |
| 2004/0172075 A1 | 9/2004 | Shafer et al. |
| 2004/0172080 A1 | 9/2004 | Stadler et al. |
| 2004/0172084 A1 | 9/2004 | Knudson et al. |
| 2004/0175399 A1 | 9/2004 | Schiffman |
| 2004/0176803 A1 | 9/2004 | Whelan et al. |
| 2004/0176805 A1 | 9/2004 | Whelan et al. |
| 2004/0182399 A1 | 9/2004 | Danek et al. |
| 2004/0186435 A1 | 9/2004 | Seward |
| 2004/0204747 A1 | 10/2004 | Kemeny et al. |
| 2004/0213813 A1 | 10/2004 | Ackerman |
| 2004/0213814 A1 | 10/2004 | Ackerman |
| 2004/0215235 A1 | 10/2004 | Jackson et al. |
| 2004/0215289 A1 | 10/2004 | Fukui |
| 2004/0215296 A1 | 10/2004 | Ganz et al. |
| 2004/0220556 A1 | 11/2004 | Cooper et al. |
| 2004/0220621 A1 | 11/2004 | Zhou et al. |
| 2004/0226556 A1 | 11/2004 | Deem et al. |
| 2004/0230251 A1 | 11/2004 | Schuler et al. |
| 2004/0230252 A1 | 11/2004 | Kullok et al. |
| 2004/0243118 A1 | 12/2004 | Ayers et al. |
| 2004/0243182 A1 | 12/2004 | Cohen et al. |
| 2004/0248188 A1 | 12/2004 | Sanders |
| 2004/0249401 A1 | 12/2004 | Rabiner et al. |
| 2004/0249416 A1 | 12/2004 | Yun et al. |
| 2004/0253274 A1 | 12/2004 | Voet |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0019346 A1 | 1/2005 | Boulis |
| 2005/0021092 A1 | 1/2005 | Yun et al. |
| 2005/0049615 A1 | 3/2005 | Cooper et al. |
| 2005/0056292 A1 | 3/2005 | Cooper |
| 2005/0059153 A1 | 3/2005 | George et al. |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0065553 A1 | 3/2005 | Ben Ezra et al. |
| 2005/0065562 A1 | 3/2005 | Rezai |
| 2005/0065567 A1 | 3/2005 | Lee et al. |
| 2005/0065573 A1 | 3/2005 | Rezai |
| 2005/0065574 A1 | 3/2005 | Rezai |
| 2005/0065575 A1 | 3/2005 | Dobak |
| 2005/0065584 A1 | 3/2005 | Schiff et al. |
| 2005/0074461 A1 | 4/2005 | Donovan |
| 2005/0076909 A1 | 4/2005 | Stahmann et al. |
| 2005/0080461 A1 | 4/2005 | Stahmann et al. |
| 2005/0085801 A1 | 4/2005 | Cooper et al. |
| 2005/0090722 A1 | 4/2005 | Perez |
| 2005/0096529 A1 | 5/2005 | Cooper et al. |
| 2005/0096644 A1 | 5/2005 | Hall et al. |
| 2005/0107783 A1 | 5/2005 | Tom et al. |
| 2005/0107829 A1 | 5/2005 | Edwards et al. |
| 2005/0107853 A1 | 5/2005 | Krespi et al. |
| 2005/0125044 A1 | 6/2005 | Tracey |
| 2005/0137518 A1 | 6/2005 | Biggs et al. |
| 2005/0137611 A1 | 6/2005 | Escudero et al. |
| 2005/0137715 A1 | 6/2005 | Phan et al. |
| 2005/0143788 A1 | 6/2005 | Yun et al. |
| 2005/0149146 A1 | 7/2005 | Boveja et al. |
| 2005/0152924 A1 | 7/2005 | Voet |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0171396 A1 | 8/2005 | Pankratov et al. |
| 2005/0177144 A1 | 8/2005 | Phan et al. |
| 2005/0177192 A1 | 8/2005 | Rezai et al. |
| 2005/0182288 A1 | 8/2005 | Zabara |
| 2005/0182393 A1 | 8/2005 | Abboud et al. |
| 2005/0183732 A1 | 8/2005 | Edwards |
| 2005/0187579 A1 | 8/2005 | Danek et al. |
| 2005/0193279 A1 | 9/2005 | Daners |
| 2005/0203503 A1 | 9/2005 | Edwards et al. |
| 2005/0222628 A1 | 10/2005 | Krakousky |
| 2005/0222635 A1 | 10/2005 | Krakovsky |
| 2005/0222651 A1 | 10/2005 | Jung, Jr. |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240176 A1 | 10/2005 | Oral et al. |
| 2005/0240241 A1 | 10/2005 | Yun et al. |
| 2005/0245992 A1 | 11/2005 | Persen et al. |
| 2005/0251128 A1 | 11/2005 | Amoah |
| 2005/0251213 A1 | 11/2005 | Freeman |
| 2005/0255317 A1 | 11/2005 | Bavaro et al. |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0015151 A1 | 1/2006 | Aldrich |
| 2006/0058692 A1 | 3/2006 | Beatty et al. |
| 2006/0058693 A1 | 3/2006 | Beatty et al. |
| 2006/0058780 A1 | 3/2006 | Edwards et al. |
| 2006/0062808 A1 | 3/2006 | Laufer et al. |
| 2006/0079887 A1 | 4/2006 | Buysse et al. |
| 2006/0084884 A1 | 4/2006 | Beatty et al. |
| 2006/0084966 A1 | 4/2006 | Maguire et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0089637 A1 | 4/2006 | Werneth et al. |
| 2006/0095032 A1 | 5/2006 | Jackson et al. |
| 2006/0100666 A1 | 5/2006 | Wilkinson et al. |
| 2006/0106361 A1 | 5/2006 | Muni et al. |
| 2006/0111755 A1 | 5/2006 | Stone et al. |
| 2006/0116749 A1 | 6/2006 | Willink et al. |
| 2006/0135953 A1 | 6/2006 | Kania et al. |
| 2006/0135984 A1 | 6/2006 | Kramer et al. |
| 2006/0135998 A1 | 6/2006 | Libbus et al. |
| 2006/0137698 A1 | 6/2006 | Danek et al. |
| 2006/0142801 A1 | 6/2006 | Demarais et al. |
| 2006/0167498 A1 | 7/2006 | DiLorenzo |
| 2006/0178703 A1 | 8/2006 | Huston et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0222667 A1 | 10/2006 | Deem et al. |
| 2006/0225742 A1 | 10/2006 | Deem et al. |
| 2006/0235474 A1 | 10/2006 | Demarais |
| 2006/0241523 A1 | 10/2006 | Sinelnikov et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247683 A1 | 11/2006 | Danek et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276807 A1 | 12/2006 | Keast et al. |
| 2006/0276852 A1 | 12/2006 | Demarais et al. |
| 2006/0278243 A1 | 12/2006 | Danek et al. |
| 2006/0278244 A1 | 12/2006 | Danek et al. |
| 2006/0280772 A1 | 12/2006 | Roschak et al. |
| 2006/0280773 A1 | 12/2006 | Roschak et al. |
| 2006/0282071 A1 | 12/2006 | Utley et al. |

(56) References Cited

U.S. PATENT DOCUMENTS

| | | |
|---|---|---|
| 2006/0287679 A1 | 12/2006 | Stone |
| 2007/0021803 A1 | 1/2007 | Deem et al. |
| 2007/0025919 A1 | 2/2007 | Deem et al. |
| 2007/0027496 A1 | 2/2007 | Parnis et al. |
| 2007/0032788 A1 | 2/2007 | Edwards et al. |
| 2007/0043342 A1 | 2/2007 | Kleinberger |
| 2007/0055328 A1 | 3/2007 | Mayse et al. |
| 2007/0060954 A1 | 3/2007 | Cameron et al. |
| 2007/0060990 A1 | 3/2007 | Satake |
| 2007/0062545 A1 | 3/2007 | Danek et al. |
| 2007/0066957 A1 | 3/2007 | Demarais et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0083239 A1 | 4/2007 | Demarais et al. |
| 2007/0093802 A1 | 4/2007 | Danek et al. |
| 2007/0093809 A1 | 4/2007 | Edwards et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106337 A1 | 5/2007 | Errico et al. |
| 2007/0106338 A1 | 5/2007 | Errico |
| 2007/0106339 A1 | 5/2007 | Errico et al. |
| 2007/0106348 A1 | 5/2007 | Laufer |
| 2007/0112349 A1 | 5/2007 | Danek et al. |
| 2007/0118184 A1 | 5/2007 | Danek et al. |
| 2007/0118190 A1 | 5/2007 | Danek et al. |
| 2007/0123922 A1 | 5/2007 | Cooper et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0173899 A1 | 7/2007 | Levin et al. |
| 2007/0191902 A1 | 8/2007 | Errico et al. |
| 2007/0197896 A1 | 8/2007 | Moll et al. |
| 2007/0203549 A1 | 8/2007 | Demarais et al. |
| 2007/0225768 A1 | 9/2007 | Dobak, III |
| 2007/0232896 A1 | 10/2007 | Gilboa et al. |
| 2007/0239256 A1 | 10/2007 | Weber et al. |
| 2007/0244479 A1 | 10/2007 | Beatty et al. |
| 2007/0250050 A1 | 10/2007 | Lafontaine |
| 2007/0255270 A1 | 11/2007 | Carney |
| 2007/0255304 A1 | 11/2007 | Roschak et al. |
| 2007/0265639 A1 | 11/2007 | Danek et al. |
| 2007/0265687 A1 | 11/2007 | Deem et al. |
| 2007/0267011 A1 | 11/2007 | Deem et al. |
| 2007/0276362 A1 | 11/2007 | Rioux et al. |
| 2008/0004596 A1 | 1/2008 | Yun et al. |
| 2008/0021274 A1 | 1/2008 | Bayer et al. |
| 2008/0021369 A1 | 1/2008 | Deem et al. |
| 2008/0051839 A1 | 2/2008 | Libbus et al. |
| 2008/0086107 A1 | 4/2008 | Roschak |
| 2008/0097139 A1 | 4/2008 | Clerc et al. |
| 2008/0097422 A1 | 4/2008 | Edwards et al. |
| 2008/0097424 A1 | 4/2008 | Wizeman et al. |
| 2008/0125772 A1 | 5/2008 | Stone et al. |
| 2008/0147137 A1 | 6/2008 | Cohen et al. |
| 2008/0154258 A1 | 6/2008 | Chang et al. |
| 2008/0161801 A1 | 7/2008 | Steinke et al. |
| 2008/0183248 A1 | 7/2008 | Rezai et al. |
| 2008/0188912 A1 | 8/2008 | Stone et al. |
| 2008/0188913 A1 | 8/2008 | Stone et al. |
| 2008/0194956 A1 | 8/2008 | Aldrich et al. |
| 2008/0208305 A1 | 8/2008 | Rezai et al. |
| 2008/0213331 A1 | 9/2008 | Gelfand et al. |
| 2008/0234564 A1 | 9/2008 | Beatty et al. |
| 2008/0243112 A1 | 10/2008 | De Neve |
| 2008/0255449 A1 | 10/2008 | Warnking et al. |
| 2008/0255642 A1 | 10/2008 | Zarins et al. |
| 2008/0262489 A1 | 10/2008 | Steinke |
| 2008/0275445 A1 | 11/2008 | Kelly et al. |
| 2008/0302359 A1 | 12/2008 | Loomas et al. |
| 2008/0306570 A1 | 12/2008 | Rezai et al. |
| 2008/0312543 A1 | 12/2008 | Laufer et al. |
| 2008/0312725 A1 | 12/2008 | Penner |
| 2008/0319350 A1 | 12/2008 | Wallace et al. |
| 2009/0018473 A1 | 1/2009 | Aldrich et al. |
| 2009/0018538 A1 | 1/2009 | Webster et al. |
| 2009/0030477 A1 | 1/2009 | Jarrard |
| 2009/0036948 A1 | 2/2009 | Levin et al. |
| 2009/0043301 A1 | 2/2009 | Jarrard et al. |
| 2009/0043302 A1 | 2/2009 | Ford et al. |
| 2009/0048593 A1 | 2/2009 | Ganz et al. |
| 2009/0060953 A1 | 3/2009 | Sandars |
| 2009/0062873 A1 | 3/2009 | Wu et al. |
| 2009/0069797 A1 | 3/2009 | Danek et al. |
| 2009/0076409 A1 | 3/2009 | Wu et al. |
| 2009/0076491 A1 | 3/2009 | Roschak et al. |
| 2009/0112203 A1 | 4/2009 | Danek et al. |
| 2009/0124883 A1 | 5/2009 | Wibowo et al. |
| 2009/0131765 A1 | 5/2009 | Roschak et al. |
| 2009/0131928 A1 | 5/2009 | Edwards et al. |
| 2009/0131930 A1 | 5/2009 | Gelbart et al. |
| 2009/0143678 A1 | 6/2009 | Keast et al. |
| 2009/0143705 A1 | 6/2009 | Danek et al. |
| 2009/0143776 A1 | 6/2009 | Danek et al. |
| 2009/0143831 A1 | 6/2009 | Huston et al. |
| 2009/0155336 A1 | 6/2009 | Rezai |
| 2009/0177192 A1 | 7/2009 | Rioux et al. |
| 2009/0192505 A1 | 7/2009 | Askew et al. |
| 2009/0192508 A1 | 7/2009 | Laufer et al. |
| 2009/0204005 A1 | 8/2009 | Keast et al. |
| 2009/0204119 A1 | 8/2009 | Bleich et al. |
| 2009/0227885 A1 | 9/2009 | Lowery et al. |
| 2009/0227980 A1 | 9/2009 | Kangas et al. |
| 2009/0232850 A1 | 9/2009 | Manack et al. |
| 2009/0248011 A1 | 10/2009 | Hlavka et al. |
| 2009/0254079 A1 | 10/2009 | Edwards et al. |
| 2009/0254142 A1 | 10/2009 | Edwards et al. |
| 2009/0259274 A1 | 10/2009 | Simon et al. |
| 2009/0275840 A1 | 11/2009 | Roschak et al. |
| 2009/0275878 A1 | 11/2009 | Cambier et al. |
| 2009/0281593 A9 | 11/2009 | Errico et al. |
| 2009/0287087 A1 | 11/2009 | Gwerder et al. |
| 2009/0306644 A1 | 12/2009 | Mayse et al. |
| 2009/0318904 A9 | 12/2009 | Cooper et al. |
| 2009/0319002 A1 | 12/2009 | Simon et al. |
| 2010/0003282 A1 | 1/2010 | Deem et al. |
| 2010/0004648 A1 | 1/2010 | Edwards et al. |
| 2010/0010564 A1 | 1/2010 | Simon et al. |
| 2010/0016709 A1 | 1/2010 | Gilboa et al. |
| 2010/0042089 A1 | 2/2010 | Soltesz et al. |
| 2010/0049031 A1 | 2/2010 | Fruland et al. |
| 2010/0049186 A1 | 2/2010 | Ingle et al. |
| 2010/0049188 A1 | 2/2010 | Nelson et al. |
| 2010/0057178 A1 | 3/2010 | Simon |
| 2010/0063495 A1 | 3/2010 | Edwards et al. |
| 2010/0070004 A1 | 3/2010 | Hlavka et al. |
| 2010/0076518 A1 | 3/2010 | Hlavka et al. |
| 2010/0087783 A1 | 4/2010 | Weber et al. |
| 2010/0087809 A1 | 4/2010 | Edwards et al. |
| 2010/0094231 A1 | 4/2010 | Bleich et al. |
| 2010/0114087 A1 | 5/2010 | Edwards et al. |
| 2010/0116279 A9 | 5/2010 | Cooper |
| 2010/0125239 A1 | 5/2010 | Perry et al. |
| 2010/0130892 A1 | 5/2010 | Warnking |
| 2010/0137860 A1 | 6/2010 | Demarais et al. |
| 2010/0145427 A1 | 6/2010 | Gliner et al. |
| 2010/0152835 A1 | 6/2010 | Orr |
| 2010/0160906 A1 | 6/2010 | Jarrard |
| 2010/0160996 A1 | 6/2010 | Simon et al. |
| 2010/0174340 A1 | 7/2010 | Simon |
| 2010/0179424 A1 | 7/2010 | Warnking et al. |
| 2010/0185190 A1 | 7/2010 | Danek et al. |
| 2010/0191089 A1 | 7/2010 | Stebler et al. |
| 2010/0204689 A1 | 8/2010 | Danek et al. |
| 2010/0222851 A1 | 9/2010 | Deem et al. |
| 2010/0228318 A1 | 9/2010 | Errico et al. |
| 2010/0241188 A1 | 9/2010 | Errico et al. |
| 2010/0249873 A1 | 9/2010 | Errico |
| 2010/0256629 A1 | 10/2010 | Wylie et al. |

(56) References Cited

U.S. PATENT DOCUMENTS

| | | |
|---|---|---|
| 2010/0256630 A1 | 10/2010 | Hamilton, Jr. et al. |
| 2010/0268222 A1 | 10/2010 | Danek et al. |
| 2010/0298905 A1 | 11/2010 | Simon |
| 2010/0305463 A1 | 12/2010 | Macklem et al. |
| 2010/0318020 A1 | 12/2010 | Atanasoska et al. |
| 2010/0331776 A1 | 12/2010 | Salahieh et al. |
| 2011/0004148 A1 | 1/2011 | Ishii |
| 2011/0015548 A1 | 1/2011 | Aldrich et al. |
| 2011/0028898 A1 | 2/2011 | Clark, III et al. |
| 2011/0046432 A1 | 2/2011 | Simon et al. |
| 2011/0060380 A1 | 3/2011 | Gelfand et al. |
| 2011/0079230 A1 | 4/2011 | Danek et al. |
| 2011/0093032 A1 | 4/2011 | Boggs, II et al. |
| 2011/0098762 A1 | 4/2011 | Rezai |
| 2011/0112400 A1 | 5/2011 | Emery et al. |
| 2011/0112521 A1 | 5/2011 | DeLonzor et al. |
| 2011/0118725 A1 | 5/2011 | Mayse et al. |
| 2011/0125203 A1 | 5/2011 | Simon et al. |
| 2011/0125213 A1 | 5/2011 | Simon et al. |
| 2011/0130708 A1 | 6/2011 | Perry et al. |
| 2011/0137284 A1 | 6/2011 | Arora et al. |
| 2011/0144630 A1 | 6/2011 | Loeb |
| 2011/0146673 A1 | 6/2011 | Keast et al. |
| 2011/0146674 A1 | 6/2011 | Roschak |
| 2011/0152855 A1 | 6/2011 | Mayse et al. |
| 2011/0152967 A1 | 6/2011 | Simon et al. |
| 2011/0152974 A1 | 6/2011 | Rezai et al. |
| 2011/0166499 A1 | 7/2011 | Demarais et al. |
| 2011/0166565 A1 | 7/2011 | Wizeman et al. |
| 2011/0172655 A1 | 7/2011 | Biggs et al. |
| 2011/0172658 A1 | 7/2011 | Gelbart et al. |
| 2011/0178569 A1 | 7/2011 | Parnis et al. |
| 2011/0184330 A1 | 7/2011 | Laufer et al. |
| 2011/0190569 A1 | 8/2011 | Simon et al. |
| 2011/0196288 A1 | 8/2011 | Kaplan et al. |
| 2011/0202098 A1 | 8/2011 | Demarais et al. |
| 2011/0224768 A1 | 9/2011 | Edwards |
| 2011/0230701 A1 | 9/2011 | Simon et al. |
| 2011/0230938 A1 | 9/2011 | Simon et al. |
| 2011/0245756 A1 | 10/2011 | Arora et al. |
| 2011/0251592 A1 | 10/2011 | Biggs et al. |
| 2011/0257622 A1 | 10/2011 | Salahieh et al. |
| 2011/0257647 A1 | 10/2011 | Mayse et al. |
| 2011/0263960 A1 | 10/2011 | Mitchell |
| 2011/0264086 A1 | 10/2011 | Ingle |
| 2011/0270249 A1 | 11/2011 | Utley et al. |
| 2011/0276107 A1 | 11/2011 | Simon et al. |
| 2011/0276112 A1 | 11/2011 | Simon et al. |
| 2011/0282229 A1 | 11/2011 | Danek et al. |
| 2011/0282418 A1 | 11/2011 | Saunders et al. |
| 2011/0301587 A1 | 12/2011 | Deem et al. |
| 2011/0301664 A1 | 12/2011 | Rezai |
| 2011/0301679 A1 | 12/2011 | Rezai et al. |
| 2011/0306851 A1 | 12/2011 | Wang |
| 2011/0306904 A1 | 12/2011 | Jacobson et al. |
| 2011/0306997 A9 | 12/2011 | Roschak et al. |
| 2011/0319958 A1 | 12/2011 | Simon et al. |
| 2012/0004656 A1 | 1/2012 | Jackson et al. |
| 2012/0015019 A1 | 1/2012 | Pacetti et al. |
| 2012/0016256 A1 | 1/2012 | Mabary et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0029500 A1 | 2/2012 | Jenson |
| 2012/0029512 A1 | 2/2012 | Willard et al. |
| 2012/0029591 A1 | 2/2012 | Simon et al. |
| 2012/0029601 A1 | 2/2012 | Simon et al. |
| 2012/0041412 A1 | 2/2012 | Roth et al. |
| 2012/0041509 A1 | 2/2012 | Knudson et al. |
| 2012/0071870 A1 | 3/2012 | Salahieh et al. |
| 2012/0078096 A1 | 3/2012 | Krolik et al. |
| 2012/0083734 A1 | 4/2012 | Ayres et al. |
| 2012/0089078 A1 | 4/2012 | Deem et al. |
| 2012/0089138 A1 | 4/2012 | Edwards et al. |
| 2012/0101326 A1 | 4/2012 | Simon et al. |
| 2012/0101413 A1 | 4/2012 | Beetel et al. |
| 2012/0109278 A1 | 5/2012 | Sih |
| 2012/0143132 A1 | 6/2012 | Orlowski |
| 2012/0143177 A1 | 6/2012 | Avitall |
| 2012/0143179 A1 | 6/2012 | Avitall |
| 2012/0143181 A1 | 6/2012 | Demarais et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165803 A1 | 6/2012 | Bencini et al. |
| 2012/0184801 A1 | 7/2012 | Simon et al. |
| 2012/0185020 A1 | 7/2012 | Simon et al. |
| 2012/0191081 A1 | 7/2012 | Markowitz |
| 2012/0191082 A1 | 7/2012 | Markowitz |
| 2012/0197100 A1 | 8/2012 | Razavi et al. |
| 2012/0197246 A1 | 8/2012 | Mauch |
| 2012/0197251 A1 | 8/2012 | Edwards et al. |
| 2012/0203067 A1 | 8/2012 | Higgins et al. |
| 2012/0203216 A1 | 8/2012 | Mayse et al. |
| 2012/0203222 A1 | 8/2012 | Mayse et al. |
| 2012/0209118 A1 | 8/2012 | Warnking |
| 2012/0209259 A1 | 8/2012 | Danek et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0232436 A1 | 9/2012 | Warnking |
| 2012/0245415 A1 | 9/2012 | Emura et al. |
| 2012/0253442 A1 | 10/2012 | Gliner et al. |
| 2012/0259263 A1 | 10/2012 | Celermajer et al. |
| 2012/0259269 A1 | 10/2012 | Meyer |
| 2012/0259326 A1 | 10/2012 | Brannan et al. |
| 2012/0265280 A1 | 10/2012 | Errico et al. |
| 2012/0289952 A1 | 11/2012 | Utley et al. |
| 2012/0290035 A1 | 11/2012 | Levine et al. |
| 2012/0294424 A1 | 11/2012 | Chin et al. |
| 2012/0296329 A1 | 11/2012 | Ng |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2012/0330298 A1 | 12/2012 | Ganz et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0035576 A1 | 2/2013 | O'Grady et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0296647 A1 | 11/2013 | Mayse et al. |
| 2013/0303948 A1 | 11/2013 | Deem et al. |
| 2013/0310822 A1 | 11/2013 | Mayse et al. |
| 2013/0345700 A1 | 12/2013 | Hlavka et al. |
| 2014/0186341 A1 | 7/2014 | Mayse |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |
| 2014/0371809 A1 | 12/2014 | Parnis et al. |
| 2015/0051597 A1 | 2/2015 | Mayse et al. |
| 2016/0038725 A1 | 2/2016 | Mayse et al. |
| 2016/0220851 A1 | 8/2016 | Mayse et al. |
| 2016/0310210 A1 | 10/2016 | Harshman et al. |
| 2017/0014571 A1 | 1/2017 | Deem et al. |
| 2018/0028748 A1 | 2/2018 | Deem et al. |
| 2018/0199993 A1 | 7/2018 | Mayse et al. |
| 2019/0105102 A1 | 4/2019 | Mayse et al. |
| 2019/0142510 A1 | 5/2019 | Mayse et al. |
| 2019/0142511 A1 | 5/2019 | Wahr et al. |
| 2019/0151018 A1 | 5/2019 | Mayse et al. |
| 2020/0001081 A1 | 1/2020 | Hlavka et al. |
| 2020/0060750 A1 | 2/2020 | Kaveckis et al. |
| 2020/0085495 A1 | 3/2020 | Dimmer et al. |
| 2020/0222114 A1 | 7/2020 | Johnson et al. |

(56) References Cited

U.S. PATENT DOCUMENTS

| | | |
|---|---|---|
| 2020/0268436 A1 | 8/2020 | Mayse |
| 2020/0360677 A1 | 11/2020 | Deem et al. |

FOREIGN PATENT DOCUMENTS

| | | |
|---|---|---|
| CN | 101115448 B | 5/2010 |
| DE | 19529634 A1 | 2/1997 |
| DE | 19952505 A1 | 5/2001 |
| EP | 0189329 A3 | 6/1987 |
| EP | 0286145 A2 | 10/1988 |
| EP | 0280225 A3 | 3/1989 |
| EP | 0286145 A3 | 10/1990 |
| EP | 0282225 B1 | 6/1992 |
| EP | 0643982 A1 | 3/1995 |
| EP | 0908713 A1 | 4/1999 |
| EP | 1143864 A2 | 10/2001 |
| EP | 1271384 A1 | 1/2003 |
| EP | 1281366 A2 | 2/2003 |
| EP | 0908150 B1 | 5/2003 |
| EP | 0768091 B1 | 7/2003 |
| EP | 1326548 A1 | 7/2003 |
| EP | 1326549 A1 | 7/2003 |
| EP | 1400204 A1 | 3/2004 |
| EP | 1297795 B1 | 8/2005 |
| EP | 1588662 A2 | 10/2005 |
| FR | 2659240 B1 | 7/1997 |
| GB | 2233293 A | 1/1991 |
| JP | S59167707 A | 9/1984 |
| JP | H07289557 A | 11/1995 |
| JP | H0947518 A | 2/1997 |
| JP | H09243837 A | 9/1997 |
| JP | H1026709 A | 1/1998 |
| RU | 2053814 C1 | 2/1996 |
| RU | 2091054 C1 | 9/1997 |
| SU | 545358 A1 | 2/1977 |
| WO | WO-8911311 A1 | 11/1989 |
| WO | WO-9301862 A1 | 2/1993 |
| WO | WO-9316632 A1 | 9/1993 |
| WO | WO-9407446 A1 | 4/1994 |
| WO | WO-9501075 A1 | 1/1995 |
| WO | WO-9502370 A2 | 1/1995 |
| WO | WO-9510322 A1 | 4/1995 |
| WO | WO-9604860 A1 | 2/1996 |
| WO | WO-9610961 A1 | 4/1996 |
| WO | WO-9725917 A1 | 7/1997 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9818391 A1 | 5/1998 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9932040 A1 | 7/1999 |
| WO | WO-9942047 A1 | 8/1999 |
| WO | WO-9964109 A1 | 12/1999 |
| WO | WO-0010598 A2 | 3/2000 |
| WO | WO-0051510 A1 | 9/2000 |
| WO | WO-0062699 A2 | 10/2000 |
| WO | WO-0066017 A1 | 11/2000 |
| WO | WO-0100114 A1 | 1/2001 |
| WO | WO-0103642 A1 | 1/2001 |
| WO | WO-0170114 A1 | 9/2001 |
| WO | WO-0189526 A1 | 11/2001 |
| WO | WO-0205720 A1 | 1/2002 |
| WO | WO-0205868 A2 | 1/2002 |
| WO | WO-0232333 A1 | 4/2002 |
| WO | WO-0232334 A1 | 4/2002 |
| WO | WO-03073358 A2 | 9/2003 |
| WO | WO-03088820 A2 | 10/2003 |
| WO | WO-2004078252 A2 | 9/2004 |
| WO | WO-2004082736 A2 | 9/2004 |
| WO | WO-2004101028 A2 | 11/2004 |
| WO | WO-2005006963 A2 | 1/2005 |
| WO | WO-2005006964 A2 | 1/2005 |
| WO | WO-2006053308 A2 | 5/2006 |
| WO | WO-2006053309 A2 | 5/2006 |
| WO | WO-2006116198 A2 | 11/2006 |
| WO | WO-2007058780 A2 | 5/2007 |
| WO | WO-2007061982 A1 | 5/2007 |
| WO | WO-2007092062 A1 | 8/2007 |
| WO | WO-2007094828 A2 | 8/2007 |
| WO | WO-2007143665 A2 | 12/2007 |
| WO | WO-2008005953 A2 | 1/2008 |
| WO | WO-2008024220 A1 | 2/2008 |
| WO | WO-2008051706 A2 | 5/2008 |
| WO | WO-2008063935 A2 | 5/2008 |
| WO | WO-2009009236 A1 | 1/2009 |
| WO | WO-2009015278 A1 | 1/2009 |
| WO | WO-2009082433 A2 | 7/2009 |
| WO | WO-2009126383 A2 | 10/2009 |
| WO | WO-2009137819 A1 | 11/2009 |
| WO | WO-2010110785 A1 | 9/2010 |
| WO | WO-2011060200 A1 | 5/2011 |

OTHER PUBLICATIONS

Accad M., "Single-Step Renal Denervation with the OneShotTM Ablation System," Presentation at the Leipzig Interventional Course 2012 in Leipzig, Germany, Jan. 26, 2012, 11 pages.

Ahnert-Hilger., et al., "Introduction of Macromolecules into Bovine Adrenal-Medullary Chromaffin Cells and Rat Pheochromocytoma Cells (PC12) by Permeabilization with Streptolysin O: Inhibitory Effect of Teanus Toxin on Catecholamine Secretion," J. Neurochem, Jun. 1989, vol. 52 (6), pp. 1751-1758.

An S S., et al., "Airway Smooth Muscle Dynamics; A Common Pathway of Airway Obstruction in Asthma," European Respiratory Journal, 2007, vol. 29 (5), pp. 834-860.

Application and File history for U.S. Appl. No. 12/944,666, filed Nov. 11, 2010. Inventors: Mayse et al.

Application and File history for U.S. Appl. No. 14/541,931, filed Nov. 14, 2010. Inventors: Mayse et al.

Application and File history for U.S. Appl. No. 15/596,192, filed May 16, 2017. Inventors: Mayse et al.

Awadh N., et al., "Airway Wall Thickness in Patients with Near Fatal Asthma and Control Groups: Assessment with High Resolution Computed Tomographic Scanning," Thorax, 1998, vol. 53, pp. 248-253.

Babichev., et al., "Clinico-Morphological Comparisons in Patients with Bronchial Asthma after Denervation of the Lungs," Sov Med, 1985, vol. 12, pp. 13-16.

Babichev., et al., "Long-term Results of Surgical Treatment of Bronchial Asthma Based on Adaptive Response," Khirurgiia (Mosk), 1993, vol. 4, pp. 5-11.

Babichev., et al., "Partial Deneration of the Lungs in Bronchial Asthma," Khirurgiia (Mosk), 1985, vol. 4, pp. 31-35.

Barlaw., "Surgical Treatment of Asthma," Postgrad Med. Journal, 1949, vol. 25, pp. 193-196.

Bel E H., "Hot Stuff: Bronchial Thermoplasty for Asthma," American Journal of Respiratory and Critical Care Medicine, 2006, vol. 173, pp. 941-942.

Bertog S., "Covidien-Maya: OneShot.TM.," presentation at the 2012 Congenital & Structural Interventions Congress in Frankfurt, Germany, Jun. 28, 2012, 25 pages.

Bester., et al., "Recovery of C-Fiber-Induced Extravasation Following Peripheral Nerve Injury in the Rat," Experimental Neurology, 1998, vol. 154, pp. 628-636.

Bigalke., et al., "Clostridial Neurotoxins," Handbook of Experimental Pharmacology (Aktories, K., and Just, I., eds), 2000, vol. 145, pp. 407-443.

Bittner., et al., "Isolated Light Chains of Botulinum Neurotoxins Inhibit Exocytosis," The Journal of Biological Chemistry, 1989, vol. 264(18), pp. 10354-10360.

(56) References Cited

OTHER PUBLICATIONS

Blindt., et al., "Development of a New Biodegradable Intravascular Polymer Stent with Simultaneous Incorporation of Bioactive Substances," The International Journal of Artificial Organs, 1999, vol. 22 (12), pp. 843-853.

Boxem V TJM., et al., "Tissue Effects of Bronchoscopic Electrocautery," Chest, Mar. 2000, vol. 117(3), pp. 887-891.

Bradley., et al., "Effect of Vagotomy on the Breathing Pattern and Exercise Ability in Emphysematous Patients," Clinical Science, 1982, vol. 62, pp. 311-319.

Breekveldt-Postma., et al., "Enhanced Persistence with Tiotropium Compared with Other Respiratory Drugs in COPD," Respiratory Medicine, 2007, vol. 101, pp. 1398-1405.

Brody., et al., "Mucociliary Clearance After Lung Denervation and Bronchial Transection," J Applied Physiology, 1972, vol. 32 (2), pp. 160-164.

Brown R H., et al., "In Vivo Evaluation of the Effectiveness of Bronchial Thermoplasty with Computed Tomography," Journal of Applied Physiology, 2005, vol. 98, pp. 1603-1606.

Buzzi., "Diphtheria Toxin Treatment of Human Advanced Cancer," Cancer Research, 1982, vol. 42, pp. 2054-2058.

Canning., et al., "Reflex Mechanisms in Gastroesophageal Reflux Disease and Asthma," The American Journal of Medicine, 2003, vol. 115 (3A), pp. 45S-48S.

Canning., "Reflex Regulation of Airway Smooth Muscle Tone," J Appl. Physiol, 2006, vol. 101, pp. 971-985.

Castro M., et al., "Effectiveness and Safety of Bronchial Thermoplasty in the Treatment of Severe Asthma: a Multicenter, Randomized, Double-Blind, Sham-Controlled Clinical Trial," American Journal of Respiratory and Critical Care Medicine, 2010, vol. 181, pp. 116-124.

Chaddock., et al., "Expression and Purification of Catalytically Active, Non-Toxic Endopeptidase Derivatives of Clostridium Botulinum Toxin Type A," Protein Expression and Purification, Jul. 2002, vol. 25 (2), pp. 219-228.

Chang., "Cell Poration and Cell Fusion Using an Oscillating Electric Field," Biophys. J, 1989, vol. 56 (4), pp. 641-652.
Chernyshova., et al., "The Effect of Low-Energy Laser Radiation in the Infrared Spectrum on Bronchial Patency in Children with Bronchial Asthma," Vopr Kurortol Fizioter Lech Fiz Kult, 1995, vol. 2, pp. 11-14, (6 pages of English translation).
Chhajed P., "Will There be a Role for Bronchoscopic Radiofrequency Ablation," J Bronchol, 2005, vol. 12 (3), p. 184.
Chomakov., et al., "Morphologic Studies of Bronchial Biopsies in Chronic Bronchitis Before and After Treatment," Arkh Patol, 1995, vol. 57 (6), pp. 21-25.(English Abstract and Translation, 8 pages).
Co-pending U.S. Appl. No. 09/095,323, filed Jun. 10, 1998, 26 pages.
Cox G., et al., "Asthma Control During the Year After Bronchial Thermoplasty," The New England Journal of Medicine, Mar. 29, 2007, vol. 356 (13), pp. 1327-1337.
Cox G., et al., "Bronchial Thermoplasty for Asthma," American Journal of Respiratory and Critical Care Medicine, 2006, vol. 173, pp. 965-969.
Cox G., et al., "Bronchial Thermoplasty: Long-Term Follow-up and Patient Satisfaction," 2004, 1 page.
Cox G., et al., "Bronchial Thermoplasty: One-Year Update, American Thoracic Society Annual Meeting," 2004, 1 page.
Cox G., et al., "Clinical Experience with Bronchial Thermoplasty for the Treatment of Asthma," Chest 124, 2003, p. 106S.
Cox G., et al., "Development of a Novel Bronchoscope Therapy for Asthma," Journal of Allergy and Clinical Immunology, 2003, 1 page.
Cox G., et al., "Early Clinical Experience With Bronchial Thermoplasty for the Treatment of Asthma," 2002, p. 1068.
Cox G., et al., "Impact of Bronchial Thermoplasty on Asthma Status: Interim Results From the AIR Trial," European Respiratory Society Annual Meeting, Munich, Germany, 2006, 1 page.
Cox G., et al., "Radiofrequency Ablation of Airway Smooth Muscle for Sustained Treatment of Asthma: Preliminary Investigations," European Respiratory Journal, 2004, vol. 24, pp. 659-663.
Crimi., et al., "Protective Effects of Inhaled Ipratropium Bromide on Bronchoconstriction Induced by Adenosine and Methacholine in Asthma," Eur Respir J, 1992, vol. 5, pp. 560-565.
Danek C J., et al., "Asthma Intervention Research (AIR) Trial Evaluating Bronchial Hermoplasty. TM.; Early Results," American Thoracic Society Annual Meeting, 2002, 1 page.
Danek C J., et al., "Bronchial Thermoplasty Reduces Canine Airway Responsiveness to Local Methacholine Challenge," American Thoracic Society Annual Meeting, 2002, 1 page.
Danek C J., et al., "Reduction in Airway Hyperesponsiveness to Methacholine by the Application of RF Energy in Dogs," J Appl Physiol, 2004, vol. 97, pp. 1946-1953.
De Paiva., et al., "Light Chain of Botulinum Neurotoxin is Active in Mammalian Motor Nerve Terminals When Delivered Via Liposomes," FEBS Lett, Dec. 1990, vol. 17:277(1-2), pp. 171-174.
Dierkesmann., et al., "Indication and Results of Endobronchial Laser Therapy," Lung, 1990, vol. 168, pp. 1095-1102.
Dimitrov-Szokodi., et al., "Lung Denervation in the Therapy of Intractable Bronchial Asthma," J. Thoracic Surg, Feb. 1957, vol. 33 (2), pp. 166-184.
Donohue., et al., "A 6-Month, Placebo-Controlled Study Comparing Lung Function and Health Status Changes in COPD Patients Treated With Tiotropium or Salmeterol," Chest, 2002, vol. 122, pp. 47-55.
"Evis Exera Bronchovideoscope Brochure," Olympus Bf-XT160, Olympus, Jun. 15, 2007, 2 pages.
Feshenko., et al., "Clinico-Morphological Comparisons in the Laser Therapy of Chronic Bronchitis Patients," Lik Sprava, 1993, vol. 10-12, pp. 75-79.(English abstract, 1 Page).
Friedman., et al., "Healthcare Costs with Tiotropium Plus Usual Care versus Usual Care Alone Following 1 Year of Treatment in Patients with Chronic Obstructive Pulmonary Disorder (COPD)," Pharmacoeconomics, 2004, vol. 22 (11), pp. 741-749.
Gaude., G.S., "Pulmonary Manifestations of Gastroesophageal Reflux Disease," Annals of Thoracic Medicine, Jul.-Sep. 2009, vol. 4 (3), pp. 115-123.
Gelb., et al., "Laser in Treatment of Lung Cancer," American College of Chest Physicians, Nov. 1984, vol. 86 (5), pp. 662-666.
George., et al., "Factors Associated With Medication Nonadherence in Patients With COPD," Chest, 2005, vol. 128, pp. 3198-3204.
Gerasin., et al., "Endobronchial Electrosurgery," Chest, 1988, vol. 93, pp. 270-274.
Gibson., et al., "Gastroesophageal Reflux Treatment for Asthma in Adults and Children," Cochrane Database Syst. Rev. 2:CD001496, 2003. (Abstract only).
Glanville., et al., "Bronchial Responsiveness after Human Heart-Lung Transplantation," Chest, 1990, vol. 97 (6), pp. 1360-1366.
Glanville., et al., "Bronchial Responsiveness to Exercise after Human Cardiopulmonary Transplantation," Chest, 1989, vol. 96 (2), pp. 281-286.
"Global Strategy for Asthma Management and Prevention," 2002, 192 pages.
Gosens., et al., "Muscarinic Receptor Signaling in the Pathophysiology of Asthma and COPD," Respiratory Research, 2006, vol. 7 (73), pp. 1-15.
Groeben., et al., "High Thoracic Epidural Anesthesia Does Not Alter Airway Resistance and Attenuates the Response to an Inhalational Provocation Test in Patients with Bronchial Hyperreactivity," Anesthesiology, 1994, vol. 81 (4), pp. 868-874.
Guarini., et al., "Efferent Vagal Fibre Stimulation Blunts Nuclear Factor-kB Activation and Protects Against Hypovolemic Hemmorrhagic Shock," Circulation, 2003, vol. 107, pp. 1189-1194.
Guzman., et al., "Bioeffects Caused by Changes in Acoustic Cavitation Bubble Density and Cell Concentration: A Unified Explanation Based on Cell-to-Bubble Ratio and Blast Radius," Ultrasound in medicine & biology, 2003, vol. 29 (8), pp. 1211-1222.
Hainsworth., et al., "Afferent Lung Denervation by Brief Inhalation of Steam," Journal of Applied Physiology, May 1972, vol. 34 (5), pp. 708-714.

(56) References Cited

OTHER PUBLICATIONS

Harding., "Recent Clinical Investigations Examining the Association of Asthma and Gastroesophageal Reflux," The American Journal of Medicine, 2003, vol. 115 (Suppl 3A), pp. 39S-44S. (Abstract only).
Hiraga., "Experimental surgical therapy of bronchial asthma. The effect of denervation in dogs," Nihon Kyobu Shikkan Gakkai Zasshi, 1981, vol. 19 (1), pp. 46-56.
Hoffmann., et al., "Inhibition of Histamine-Induced Bronchoconstriction in Guinea Pig and Swine by Pulsed Electrical Vagus Nerve Stimulation," Neuromodulation: Technology at the Neural Interface, 2009, pp. 1-9.
Hogg J.C., et a., "The Pathology of Asthma," APMIS, Oct. 1997, vol. 105 (10), pp. 735-745.
Hooper., et al., "Endobronchial Electrocautery," Chest, 1985, vol. 87 (6), pp. 712-714.
Ivanyuta O M., et al., "Effect of Low-Power Laser Irradiation of Bronchia Mucosa on the State of Systemic and Local Immunity in Patients with Chronic Bronchitis," Problemy Tuberkuleza, 1991, vol. 6, pp. 26-29.
James., et al., "The Mechanics of Airway Narrowing in Asthma," The American Review of Respiratory Disease, 1989, vol. 139, pp. 242-246.
Jammes., et al., "Assessment of the Pulmonary Origin of Bronchoconstrictor Vagal Tone," The Journal of physiology, 1979, vol. 291, pp. 305-316.
Janssen L. J., "Asthma therapy: how far have we come, why did we fail and where should we go next?," European Respiratory Journal, 2009, vol. 33, pp. 11-20.
Jiang., et al., "Effects of Antireflux Treatment on Bronchial Hyperresponsiveness and Lung Function in Asthmatic Patients with Gastroesophageal Reflux Disease," World Journal of Gastroenterology, 2003, vol. 9, pp. 1123-1125. (Abstract only).
Johnson S R., et al., "Synthetic Functions of Airway Smooth Muscle in Asthma," Trends in Pharmacological Sciences, Aug. 1997, vol. 18 (8), pp. 288-292.
Karashurov., et al., "Electrostimulation in the Therapy of Bronchial Asthma," Klin Med (Mosk), 2001, vol. 79 (11), pp. 39-41.
Karashurov., et al., "Radiofrequency Electrostimulation of Carotid Sinus Nerves for the treatment of Bronchial Asthma," Khirurgiia (Mosk), 1999, vol. 12, pp. 4-6.
Khmel'Kova et al., "Does laser irridation affect bronchial obstruction? ," Probl Tuberk, 1995, vol. 3, pp. 41-42 (Abstract only).
Khoshoo., et al., "Role of Gastroesophageal Reflux in Older Children with Persistent Asthma," Chest, 2003, vol. 123, pp. 1008-1013. (Abstract only).
Kiljander., "The Role of Proton Pump Inhibitors in the Management of Gastroesophageal Reflux Disease-Related Asthma and Chronic Cough, " The American Journal of Medicine, 2003, vol. 115 (Suppl 3A), pp. 65S-71S. (Abstract only.).
Kistner., et al., "Reductive Cleavage of Tetanus Toxin and Botulinum Neurotoxin A by the Thioredoxin System from Brain," Naunyn-Schmiedebergs Arch Pharmacal, Feb. 1992, vol. 345 (2), pp. 227-234.
Kitamura S., "Color Atlas of Clinical Application of Fiberoptic Bronchoscopy," 1990, Year Book Medical Publishers, p. 17.
Kletskin., et al., "Value of Assessing the Autonomic Nervous System in Bronchial Asthma in Selecting the Surgical Treatment Method," Khirurgiia (Mosk), 1987, vol. 7, pp. 91-95.
Kliachkin., et al., "Bronchoscopy in the Treatment of Bronchial Asthma of Infectious Allergic Origin," Terapeuticheskiĭ arkhiv, 1982, vol. 54 (4), pp. 76-79.
Korochkin., et al., "Use of a Helium-Neon Laser in Combined Treatment of Bronchial Asthma," New Developments in Diagnostics and Treatment, 1990, 9 pages.
Korpela., et al., "Comparison of Tissue Reactions in the Tracheal Mucosa Surrounding a Bioabsorbable and Silicone Airway Stents," Annals of Thoracic Surgery, 1998, vol. 66, pp. 1772-1776.
Kozaki., et al., "New Surgical Treatment of Bronchial Asthma—Denervation of the Hilus Pulmonis (2)," Nippon Kyobu Geka Gakkai Zasshi, 1974, vol. 22 (5), pp. 465-466.
Kraft M., "The Distal Airways: Are they Important in Asthma?," European Respiratory, 1999, pp. 1403-1417.
Kreitman., "Taming Ricin Toxin," Nature Biotechnology, 2003, vol. 21, pp. 372-374.
Kuntz., "The Autonomic Nervous System in Relation to the Thoracic Viscera," Chest, 1944, vol. 10, pp. 1-18.
Lavioletts et al., "Asthma Intervention Research (AIR) Trial: Early Safety Assessment of Bronchial Thermoplasty," 2004, 1 page.
Leff., et al., "Bronchial Thermoplasty Alters Airway Smooth Muscle and Reduces Responsiveness in Dogs; A Possible Procedure for the Treatment of Asthma," American Thoracic Society Annual Meeting, 2002, 1 page.
Lennerz., et al., "Electrophysiological Characterization of Vagal Afferents Relevant to Mucosal Nociception in the Rat Upper Oesophagus," The Journal of physiology, 2007, vol. 582 (1), pp. 229-242.
Levin., "The Treatment of Bronchial Asthma by Dorsal Sympathectomy," Annals of Surgery, 1935, vol. 102 (2), pp. 161-170.
Lim E E., et al., "Botulinum Toxin: A Novel Therapeutic Option for Bronchial Asthma?, " Medical Hypotheses, 2006, vol. 66, pp. 915-919.
Liou., et al., "Causative and Contributive Factors to Asthmas Severity and Patterns of Medication Use in Patients Seeking Specialized Asthma Care," Chest, 2003, vol. 124, pp. 1781-1788. (Abstract only).
Lokke., et al., "Developing COPD: A 25 Year Follow Up Study of the General Population," Thorax, 2006, vol. 61, pp. 935-939.
Lombard., et al., "Histologic Effects of Bronchial Thermoplasty of Canine and Human Airways," American Thoracic Society Annual Meeting, 2002, 1 page.
Macklem P T., "Mechanical Factors Determining Maximum Bronchoconstriction, European Respiratory Journal," Jun. 1989, vol. 6, pp. 516s-519s.
Maesen., et al., "Tiotropium Bromide, A New Long-Acting Antimuscarinic Bronchodilator: A Pharmacodynamic Study in Patients with Chronic Obstructive Pulmonary Disease (COPD)," The European Respiratory Journal, 1995, vol. 8, pp. 1506-1513.
Magnussen., et al., "Effect of Inhaled Ipratropium Bromide on the Airway Response to Methacholine, Histamine, and Exercise in Patients with Mild Bronchial Asthma," Respiration, 1992, vol. 59, pp. 42-47.
Maltais., et al., "Improvements in Symptom-Limited Exercise Performance Over 8 h With Once-Daily Tiotropium in Patients With COPD," Chest, 2005, vol. 128, pp. 1168-1178.
Martin N., et al., "Bronchial Thermoplasty for the Treatment of Asthma," Current Allergy and Asthma Reports, Jan. 2009, vol. 9 (1), pp. 88-95.
Mathew., et al., "Gastro-Oesophageal Reflux and Bronchial Asthma: Current Status and Future Directions," Postgraduate Medical Journal, 2004, vol. 80, pp. 701-705.
Matthias O., et al., "Fisherman's Pulmonary Diseases and Disorders," Functional Design of the Human Lung for Gas Exchange, McGraw Hill Medical, New York, Edition 4, 2008, Chapter 2(Abstract only).
Mayse M., et al., "Clinical Pearls for Bronchial Thermoplasty," J Bronchol, Apr. 2007, vol. 14 (2), pp. 115-123.
Mcevoy C E., et al., "Changing the Landscape: Bronchial Thermoplasty Offers a Novel Approach to Asthma Treatment," Advance for Managers of Respiratory Care, Oct. 24-25, 2007, pp. 22-25.
Mckay., et al., "Autocrine Regulation of Asthmatic Airway Inflammation: Role of Airway Smooth Muscle," Respiratory Research, 2002, vol. 3 (11), pp. 1-13.
Mehta., et al., "Effect of Endobronchial Radiation therapy on Malignant Bronchial Obstruction," Chest, Mar. 1990, vol. 97 (3), pp. 662-665.
Meshalkin., et al., "Partial Denervation of the Pulmonary Hilus as One of the Methods of Surgical Treatment of Bronchial Asthma," Grudnaia Khirurgiia, 1975, vol. 1, pp. 109-111.

(56) References Cited

OTHER PUBLICATIONS

Michaud G., et al., "Positioned for Success: Interest in Diagnostic and Therapeutic Bronchoscopy is Growing," Advance for Managers of Respiratory Care, Jul.-Aug. 2008, pp. 40, 42-43.
Miller J D., et al., "A Prospective Feasibility Study of Bronchial Thermoplasty in the Human Airway," 2005, vol. 127 (6), pp. 1999-2006.
Miller J D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle the appendix of the Lung," American Journal of Respiratory and Critical Care Medicine, 2004, vol. 169, pp. 787-790.
Mitzner W., "Bronchial Thermoplasty in Asthma," Allergology International, 2006, vol. 55, pp. 225-234.
Montaudon M., et al., "Assessment of Bronchial Wall Thickness and Lumen Diameter in Human Adults Using Multi-Detector Computed Tomography: Comparison with Theoretical Models," Journal of Anatomy, 2007, vol. 211, pp. 579-588.
Moore K.L., "Clinically Oriented Anatomy," Williams & Wilkins, Baltimore, 1985, 2nd edition, pp. 85 and 87(Abstract only).
Netter F H., Respiratory System: A Compilation of Paintings Depicting Anatomy and Embryology, Physiology, Pathology, Pathophysiology, and Clinical Features and Treatment of Diseases, In The CIBA Collection of Medical Illustrations M.B. Divertie, ed., Summit: New Jersey, 1979, vol. 7, pp. 119-135.
Netter F H., "The Ciba Collection of Medical Illustrations," Respiratory System, CIBA-GEIGY Corporation, West Caldwell, 1979, vol. 7, p. 23, section 1. (Abstract only).
O'Connor., et al., "Prolonged Effect of Tiotropium Bromide on Methacholine-induced Bronchoconstriction in Asthma," American Journal of Respiratory and Critical Care Medicine, 1996, vol. 154, pp. 876-880.
O'Sullivan M P., et al., "Apoptosis in the Airways: Another Balancing Act in the Epithelial Program," American Journal of Respiratory Cell and Molecular Biology, 2003, vol. 29, pp. 3-7.
Ovcharenko., et al., "Endobronchial Use Of Low-Frequency Ultrasound And Ultraviolet Laser Radiation In The Complex Treatment Of Patients With Suppurative Bronchial Diseases," Problemy Tuberkuleza, 1997, vol. 3, pp. 40-42. (Abstract only).
Overholt., "Glomectomy for Asthma," Diseases of the Chest, 1961, vol. 40, pp. 605-610.
Pavord I D., et al., "Safety and Efficacy of Bronchial Thermoplasty in Symptomatic, Severe Asthma," American Journal of Respiratory and Critical Care Medicine, 2007, vol. 176, pp. 1185-1191.
Peter K. Jeffery, "Remodeling in Asthma and Chronic Obstructive Lung Disease," American Journal of Respiratory and Critical Care Medicine, 2001, vol. 164 (10), pp. S28-S38.
Peters, et al., "Tiotropium Bromide Step-Up Therapy for Adults with Uncontrolled Asthma," New England Journal of Medicine, Oct. 28, 2010, vol. 363 (18), pp. 1715-1726.
Petrou et al., "Bronchoscopic Diathermy Resection and Stent Insertion: a Cost Effective Treatment for Tracheobronchial Obstruction," Thorax, 1993, vol. 48, pp. 1156-1159.
Polosukhin., "Dynamics of the Ultrastructural Changes in Blood and Lymphatic Capillaries of Bronchi in Inflammation and Following Endobronchial Laser Therapy," Virchows Arch, 1997, vol. 431, pp. 283-290.
Polosukhin., "Regeneration of Bronchial Epithelium of Chronic Inflammatory Changes Under Laser Treatment," Pathology, Research and Practice, 1996, vol. 192 (9), pp. 909-918.
Polosukhin., "Ultrastructural Study of the Destructive and Repair Processes in Pulmonary Inflammation and Following Endobronchial Laser Therapy," Virchows Arch, 1999, vol. 435, pp. 13-19.
Polosukhin., "Ultrastructure of the Blood and Lymphatic Capillaries of the Respiratory Tissue During Inflammation and Endobronchial Laser Therapy," Ultrastructural Pathology, 2000, vol. 24, pp. 183-189.
Provotorov V M., et al., "Clinical Efficacy of Treatment of Patients with Non-Specific Pulmonary Diseases by Using Low-Power Laser Irradiation and Performing Intrapulmonary Drug Administration," Terapevichesky Arkhiv, 1991, vol. 62, pp. 18-23.
Provotorov V.M., et al., "The Clinical Efficacy of Treating Patients with Nonspecific Lung Disease by Using Low-energy Laser Irradiation and Intrapulmonary Drug Administration," ISSN: 0040-3660, Terapeuticheskii Arkhiv (USSR), 1991, vol. 62 (12), pp. 18-23 (11 pages).
Raj., "Editorial," Pain Practice, 2004, vol. 4 (1S), pp. S1-S3.
Ramirez et al., "Sympathetomy in Bronchial Asthma," J. A. M. A., 1925, vol. 84 (26), pp. 2002-2003.
Rienhoff., et al., "Treatment of Intractable Bronchial Asthma by Bilateral Resection of the Posterior Pulmonary Plexus," Arch Surg, 1938, vol. 37 (3), pp. 456-469.
Rocha-Singh K J., "Renal Artery Denervation: A Brave New Frontier," Endovascular Today, Feb. 2012, pp. 45-53.
Rubin., et al., "Bronchial Thermoplasty Improves Asthma Status of Moderate to Severe Persistent Asthmatics Over and Above Current Standard-of-Care," American College of Chest Physicians, 2006, 2 pages.
Savchenko., et al., "Adaptation of Regulatory Physiological Systems in Surgical Treatment of Patients with Bronchial Asthma," Klin Med (Mask), 1996, vol. 74 (7), pp. 38-39.
Sengupta., "Part 1 Oral Cavity, Pharynx and Esophagus—Esophageal Sensory Physiology," GI Motility online, 2006, 17 pages.
Seow C Y., et al., "Signal Transduction in Smooth Muscle Historical Perspective on Airway Smooth Muscle: The Saga of a Frustrated Cell," Journal of applied physiology, 2001, vol. 91, pp. 938-952.
Sepulveda., et al., "Treatment of Asthmatic Bronchoconstriction by Percutaneous Low Voltage Vagal Nerve Stimulation: Case Report," Internet Journal of Asthma, Allergy, and Immunology, 2009, vol. 7 (2), 3 pages.
Shaari., et al., "Rhinorrhea is Decreased in Dogs After Nasal Application of Botulinum Toxin," Otolaryngol Head Neck Surgery, Apr. 1995, vol. 112 (4), pp. 566-571.
Sheski F D., et al., "Cryotherapy, Electrocautery, and Brachytherapy," Clinics in Chest Medicine, Mar. 1999, vol. 20 (1), pp. 123-138.
Shesterina M V., et al., "Effect of laser therapy on immunity in patients with bronchial asthma and pulmonary tuberculosis," 1993, pp. 23-26.
Shore S A., "Airway Smooth Muscle in Asthma—Not Just More of the Same," The New England Journal of Medicine, 2004, vol. 351 (6), pp. 531-532.
Sil'Vestrov., et al., "The Clinico-Pathogenetic Validation and Efficacy of the Use of Low-Energy Laser Irradiation and Glucocorticoids in the Treatment of Bronchial Asthma Patients," Department of Therapy of the Pediatric and Stomatological Faculties of the N.N. Burdenko Voronezh Medical Institute, vol. 63(11), 1991, pp. 87-92.
Simonsson., et al., "Role of Autonomic Nervous System and the Cough Reflex in the Increased Responsiveness of Airways in Patients with Obstructive Airway Disease," The Journal of Clinical Investigation, 1967, vol. 46 (11), pp. 1812-1818.
Simpson., et al., "Isolation and Characterization of the botulinum Neurotoxins," Methods Enzymol, 1988, vol. 165, pp. 76-85.
Smakov., "Denervation of the Lung in the Treatment of Bronchial Asthma," Khirurgiia (Mosk), 1982, vol. 9, pp. 117-120.
Smakov., "Pathogenetic Substantiation of Lung Denervation in Bronchial Asthma and it's Indications," Khirurgiia (Mosk), 1999, vol. 2, pp. 67-69.
Smakov., "Prognostication of the Effect of Therapeutic Bronchoscopy in Patients with Bronchial Asthma According to the State of Local Immunity," Klin Med (Mask), 1995, vol. 73 (5), pp. 76-77.
Solway J., et al., "Airway Smooth Muscle as a Target for Asthma Therapy," The New England Journal of Medicine, Mar. 29, 2007, vol. 356 (13), pp. 1367-1369.
Sontag., et al., "Asthmatics with Gastroesophageal Reflux: Long-term Results of a Randomized Trial of Medical and Surgical Antireflux Therapies," The American Journal of Gastroenterology, 2003, vol. 98, pp. 987-999. (Abstract only.).
Stein., "Possible Mechanisms of Influence of Esophageal Acid on Airway Hyperresponsiveness," The American Journal of Medicine, 2003, vol. 115 (Suppl 3A), pp. 55S-59S. (Abstract only.).

(56) References Cited

OTHER PUBLICATIONS

Sterk P J., "Heterogeneity of Airway Hyperresponsiveness: Time for Unconventional, but Traditional Studies," The American Pshychoiogical Society, 2004, pp. 2017-2018.

Sundaram, et al., "An Experimental and Theoretical Analysis of Ultrasound-Induced Permeabilization of Cell Membranes," Biophysical Journal, May 2003, vol. 84 (5), pp. 3087-3101.

Takino., et al., "Surgical Removal of the Carotid Body and its Relation to the Carotid Chemoreceptor and Baroreceptor Reflex in Asthmatics," Dis Chest, 1965, vol. 47, pp. 129-138.

Tashkin., et al., "Long-term Treatment Benefits With Tiotropium in COPD Patients With and Without Short-term Bronchodilator Responses," Chest, 2003, vol. 123, pp. 1441-1449.

Toma T P., "Brave New World for Interventional Bronchoscopy," Thorax, 2005, vol. 60, pp. 180-181.

Trow T., "Clinical Year in Review I, proceedings of the American Thoracic Society," 2006, vol. 3, pp. 553-556.

Tschumperlin D J., et al., "Chronic Effects of Mechanical Force on Airways," Annual Review of Physiology, 2006, vol. 68, pp. 563-583.

Tschumperlin D J., et al., "Mechanical Stimuli to Airway Remodeling," American Journal of Respiratory and Critical Care Medicine, 2001, vol. 164, pp. S90-S94.

Tsugeno., et al., "A Proton-Pump Inhibitor, Rabeprazole, Improves Ventilatory Function in Patients with Asthma Associated with Gastroesophageal Reflux," Scand J Gastroenterol, 2003, Vol. (38), pp. 456-461. (Abstract only).

Tsuji., et al., "Biodegradable Stents as a Platform to Drug Loading," International Journal of Cardiovascular Interventions, 2003, vol. 5(1), pp. 13-16.

Unal., et al., "Effect of Botulinum Toxin Type A on Nasal Symptoms in Patients with Allergic Rhinitis: A Double-blind, Placebo-controlled Clinical Trial," Acta Oto-Laryngologica, Dec. 2003, vol. 123 (9), pp. 1060-1063.

Unsw, "Embryo-Respiratory System," Embryology, 2007, retrieved from: http://embryology.med.unsw.edu.au/Refer/respire/select.htm on Dec. 10, 2007, 22 pages.

Urologix inc., "Cooled ThermoTherapy™" retrieved on Mar. 5, 2013, from http://www.urologix.com/cliinicians/cooled-thermotherapy.php, 2012, 2 pages.

Urologix, Inc, "CTC Advance. TM. Instructions for Use," Targis. RTM. System Manual, 2010, 8 pages.

Velden V D., et al., "Autonomic Innervation of Human Airways: Structure, Function, and Pathophysiology in Asthma," Neuroimmunomodulation, 1999, vol. 6, pp. 145-159.

Verhein., et al., "Neural Control of Airway Inflammation," Current Allergy and Asthma Reports, 2009, vol. 9, pp. 484-490.

Vincken., et al., "Improved health outcomes in patients with COPD during 1 yr's treatment with tiotropium," Eur. Respir. J., 2002, vol. 19, pp. 209-216.

Vorotnev., et al., "Treatment of Patients with Chronic Obstructive Bronchitis Using Low Energy Laser at a General Rehabilitation Center," Therapeutic Archive, 1997, vol. 3, pp. 17-19.

Wagner., et al., "Methacholine causes reflex bronchoconstriction," J. Appi. Physiol, 1999, vol. 86, pp. 294-297.

Wahidi., et al., "State of the Art: Interventional Pulmonology," American College of Chest Physicians, Jan. 2007, vol. 131 (1), pp. 261-274.

Weaver, "Electroporation: A General Phenomenon for Manipulating Cells and Tissues," Journal of Cellular Biochemistry, Apr. 1993, vol. 51(4), pp. 426-435.

Wechsler M E., "Bronchial Thermoplasty for Asthma: A Critical Review of a New Therapy," Allergy and Asthma Proceedings, Jul.-Aug. 2008, vol. 29 (4), pp. 1-6.

Wiggs B R., et al., On the Mechanism of Mucosal Folding in Normal and Asthmatic Airways, J. Appl. Physiol, Dec. 1997, vol. 83 (6), pp. 1814-1821.

Wilson K C., et al., "Flexible Bronchoscopy: Indications and contraindications," UptoDate, Nov. 12, 2010 (retrieved Sep. 30, 2012 from www.uptodate.com), 15 pages.

Wilson S R., et al., "Global assessment after bronchial thermoplasty: the patient's perspective," Journal of Outcomes Research, 2006, vol. 10, pp. 37-46.

Wirtz., et al., "Bilateral Lung Transplantation for Severe Persistent and Difficult Asthma," The Journal of Heart and Lung Transplantation, 2005, vol. 24 (10), pp. 1700-1703.

Wizeman., et al., "A Computer Model of Thermal Treatment of Airways by Radiofrequency (RF) Energy Delivery," American Thoracic Society Annual Meeting, 2007, 1 page.

NON-INVASIVE AND MINIMALLY INVASIVE DENERVATION METHODS AND SYSTEMS FOR PERFORMING THE SAME

RELATED APPLICATIONS

This application is a continuation of application Ser. No. 16/842,062, filed Apr. 7, 2020, now U.S. Pat. No. 11,712,283, Application Ser. No. 16/842,062 is a continuation of application Ser. No. 15/596,192 filed May 16, 2017, now U.S. Pat. No. 10,610,283, which in turn is a division of application Ser. No. 14/541,931 filed Nov. 14, 2014, now U.S. Pat. No. 9,649,154 issued May 16, 2017, which in turn is a continuation of application Ser. No. 12/944,666 filed Nov. 11, 2010, now U.S. Pat. No. 8,911,439 issued Dec. 16, 2014, which claims the benefit of U.S. Provisional Application No. 61/260,350 filed Nov. 11, 2009, each of which is hereby fully incorporated herein by reference.

BACKGROUND

Technical Field

The present invention generally relates to non-invasive and minimally invasive denervation methods and systems and apparatuses for performing those methods.

Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied and often include cough, breathlessness, and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

Asthma can be characterized by contraction of airway smooth muscle, smooth muscle hypertrophy, excessive mucus production, mucous gland hypertrophy, and/or inflammation and swelling of airways. These abnormalities are the result of a complex interplay of local inflammatory cytokines (chemicals released locally by immune cells located in or near the airway wall), inhaled irritants (e.g., cold air, smoke, allergens, or other chemicals), systemic hormones (chemicals in the blood such as the anti-inflammatory cortisol and the stimulant epinephrine), local nervous system input (nerve cells contained completely within the airway wall that can produce local reflex stimulation of smooth muscle cells and mucous glands and can contribute to inflammation and edema), and the central nervous system input (nervous system signals from the brain to smooth muscle cells, mucous glands and inflammatory cells carried through the vagus nerve). These conditions often cause widespread temporary tissue alterations and initially reversible airflow obstruction that may ultimately lead to permanent tissue alteration and permanent airflow obstruction that make it difficult for the asthma sufferer to breathe. Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and cough.

Emphysema is a type of COPD often characterized by the alteration of lung tissue surrounding or adjacent to the airways in the lungs. Emphysema can involve destruction of lung tissue (e.g., alveoli tissue such as the alveolar sacs) that leads to reduced gas exchange and reduced radial traction applied to the airway wall by the surrounding lung tissue. The destruction of alveoli tissue leaves areas of emphysematous lung with overly large airspaces that are devoid of alveolar walls and alveolar capillaries and are thereby ineffective at gas exchange. Air becomes "trapped" in these larger airspaces. This "trapped" air may cause over-inflation of the lung, and in the confines of the chest restricts the in-flow of oxygen rich air and the proper function of healthier tissue. This results in significant breathlessness and may lead to low oxygen levels and high carbon dioxide levels in the blood. This type of lung tissue destruction occurs as part of the normal aging process, even in healthy individuals. Unfortunately, exposure to chemicals or other substances (e.g., tobacco smoke) may significantly accelerate the rate of tissue damage or destruction. Breathlessness may be further increased by airway obstruction. The reduction of radial traction may cause the airway walls to become "floppy" such that the airway walls partially or fully collapse during exhalation. An individual with emphysema may be unable to deliver air out of their lungs due to this airway collapse and airway obstructions during exhalation.

Chronic bronchitis is a type of COPD that can be characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent. It is often difficult for a chronic bronchitis sufferer to breathe because of chronic symptoms of shortness of breath, wheezing, and chest tightness, as well as a mucus producing cough.

Different techniques can be used to assess the severity and progression of pulmonary diseases. For example, pulmonary function tests, exercise capacity, and quality of life questionnaires are often used to evaluate subjects. Pulmonary function tests involve objective and reproducible measures of basic physiologic lung parameters, such as total airflow, lung volume, and gas exchange. Indices of pulmonary function tests used for the assessment of obstructive pulmonary diseases include the forced expiratory volume in 1 second (FEV1), the forced vital capacity (FVC), the ratio of the FEV1 to FVC, the total lung capacity (TLC), airway resistance and the testing of arterial blood gases. The FEV1 is the volume of air a patient can exhale during the first second of a forceful exhalation which starts with the lungs completely filled with air. The FEV1 is also the average flow that occurs during the first second of a forceful exhalation. This parameter may be used to evaluate and determine the presence and impact of any airway obstruction. The FVC is the total volume of air a patient can exhale during a forceful exhalation that starts with the lungs completely filled with air. The FEV1/FVC is the fraction of all the air that can be exhaled during a forceful exhalation during the first second. A FEV1/FVC ratio less than 0.7 after the administration of at least one bronchodilator defines the presence of COPD. The TLC is the total amount of air within the lungs when the lungs are completely filled and may increase when air becomes trapped within the lungs of patients with obstructive lung disease. Airway resistance is defined as the pressure gradient between the alveoli and the mouth to the rate of air flow between the alveoli and the mouth. Similarly, resistance of a given airway is defined as the ratio of the pressure gradient across the given airway to the flow of air through the airway. Arterial blood gases tests measure the amount of oxygen and the amount of carbon dioxide in the blood and are the most direct method for assessing the ability of the lungs and respiratory system to bring oxygen from the air into the blood and to get carbon dioxide from the blood out of the body.

Exercise capacity tests are objective and reproducible measures of a patient's ability to perform activities. A six minute walk test (6 MWT) is an exercise capacity test in which a patient walks as far as possible over a flat surface in 6 minutes. Another exercise capacity test involves measuring the maximum exercise capacity of a patient. For example, a physician can measure the amount of power the patient can produce while on a cycle ergometer. The patient can breathe 30 percent oxygen and the work load can increase by 5-10 watts every 3 minutes.

Quality of life questionnaires assess a patient's overall health and well being. The St. George's Respiratory Questionnaire is a quality of life questionnaire that includes 75 questions designed to measure the impact of obstructive lung disease on overall health, daily life, and perceived well-being. The efficacy of a treatment for pulmonary diseases can be evaluated using pulmonary function tests, exercise capacity tests, and/or questionnaires. A treatment program can be modified based on the results from these tests and/or questionnaires.

Treatments, such as bronchial thermoplasty, involve destroying smooth muscle tone by ablating the airway wall in a multitude of bronchial branches within the lung thereby eliminating both smooth muscles and nerves in the airway walls of the lung. The treated airways are unable to respond favorably to inhaled irritants, systemic hormones, and both local and central nervous system input. Unfortunately, this destruction of smooth muscle tone and nerves in the airway wall may therefore adversely affect lung performance. For example, inhaled irritants, such as smoke or other noxious substances, normally stimulate lung irritant receptors to produce coughing and contracting of airway smooth muscle. Elimination of nerves in the airway walls removes both local nerve function and central nervous input, thereby eliminating the lung's ability to expel noxious substances with a forceful cough. Elimination of airway smooth muscle tone may eliminate the airway's ability to constrict, thereby allowing deeper penetration of unwanted substances, such as noxious substances, into the lung.

Both asthma and COPD are serious diseases with growing numbers of sufferers. Current management techniques, which include prescription drugs, are neither completely successful nor free from side effects. Additionally, many patients do not comply with their drug prescription dosage regiment. Accordingly, it would be desirable to provide a treatment which improves resistance to airflow without the need for patient compliance.

BRIEF SUMMARY

Some embodiments are directed to non-invasive or minimally invasive denervation procedures. The denervation procedures can be performed without causing trauma that results in significant recovery periods. Non-invasive denervation methods can involve delivering energy from energy sources positioned external to the subject. The energy is aimed at targeted tissue to minimize, limit, or substantially eliminate appreciable damage to non-targeted tissue. Minimally invasive denervation procedures can involve percutaneously delivering an instrument.

Denervation of hollow organs, such as the lung bronchus, can be due to the creation of lesions with radiofrequency ablation that are of a sufficient depth when generated on the outside of the organ to penetrate the adventitial tissue layers where nerve trunks are anatomically located. In the example of lung denervation, ablating nerve trunks along the outside of both the right and left main bronchi effectively disconnects airway smooth muscle which lines the inside of the lung airways and mucus producing glands located with the airways from the vagus nerve. When this occurs, airway smooth muscle relaxes and mucus production is decreased. Nervous system mediated inflammation and edema will decrease as well. These changes reduce airway obstruction for subjects with COPD, asthma, or the like. Reduced airway obstruction makes breathing easier which improves the subject's quality of life and health status. Tests and questionnaires can be used to evaluate and monitor the subject's health.

Some embodiments are directed to a percutaneously deliverable apparatus capable of performing a denervation procedure. The apparatus can ablate targeted nerve tissue to denervate at least a portion of a lung. A minimally invasive access device can be used to percutaneously deliver the apparatus and can be a needle, a trocar, a robotic catheter, a mediastinoscope, a port, or a thoracoscope. Direct or remote visualization techniques (e.g., ultrasound guidance, endoscopy, radiologic guidance, etc.) can be used to position the apparatus.

The apparatus can be an instrument insertable directly into a hollow organ (e.g., through the mouth and into the esophagus or stomach) or inserted through the instrument channel of an endoscope (e.g., gastroscope, esophagoscope, or the like). The instrument has a flexible elongate shaft that carries one or more ablation elements. The ablation elements can be energy emitters, such as electrodes. The apparatus can be delivered through an opening in the subject's chest. The instrument can be brought into direct contact with the outer surface of the bronchial tree or lung while extending through the hollow organ.

The apparatus can be an instrument insertable directly into a large peripheral artery (e.g., femoral artery, brachial artery, or the like) and advanced through the arterial tree, into the aorta, and then into one or more bronchial arteries traveling along the main stem bronchi. The instrument has a flexible elongate shaft that carries one or more ablation elements. The ablation elements can be energy emitters, such as electrodes. The bronchial arteries are often located in close proximity to the vagus nerve trunks traveling along the outside of the bronchial tree. Placement of the instrument in one or more bronchial arteries brings the instrument with its ablation elements into close proximity to the vagus nerve trunks traveling along the outside of the bronchial tree. Advancement of the instrument and placement in the bronchial arteries can be guided by a variety of imaging modalities (e.g., fluoroscopy, ultrasound, CT scans, or the like).

In some embodiments, an instrument has an activatable section capable of intimately contacting a surface of an airway (either an outer surface or an inner surface). The activatable section can include one or more selectively activatable energy emitters, ablation elements, or the like. The activatable section can preferentially treat the posterior portion of the main lung airways or other targeted region(s) of airways.

A system for treating a subject includes an extraluminal elongate assembly dimensioned to move around the outside of the airway of a bronchial tree and an access device. The elongate assembly is adapted to attenuate signals transmitted by nerve tissue, such as nerve tissue of nerve trunks, while not irreversibly damaging adjacent anatomical structures. The elongate assembly can include at least one ablation element, which includes one or more electrodes operable to output radiofrequency energy.

Some methods involve minimally invasive denervation of at least a portion of a lung. The method comprises damaging nerve tissue of a first main bronchus to substantially prevent nervous system signals from traveling to most or substantially all distal bronchial branches connected to the first main bronchus. The nerve tissue, in certain embodiments, is positioned between a trachea and a lung through which the bronchial branches extend. The airway can remain intact while the nerve tissue is damaged.

The method, in some embodiments, further includes damaging nerve tissue of a second main bronchus to substantially prevent nervous system signals from traveling to most or substantially all distal bronchial branches connected to the second main bronchus. An apparatus used to damage the nerve tissue can be percutaneously delivered with the assistance of sonographic guidance, radiologic guidance, robotic guidance, mediastinoscopic guidance, thoracoscopic guidance, or other minimally invasive surgery visualization techniques.

In some embodiments, a method for treating a subject includes moving a tip of an instrument through at least a portion of a subject's skin to position the instrument next to nerve tissue. A desired amount of nerve tissue can then be damaged using the instrument. Some methods include damaging nerve tissue along a right main bronchus and ablating nerve tissue along the left main bronchus to denervate a significant portion of the bronchial tree. In other embodiments, denervating a portion of the bronchial tree comprises destroying at least one nerve trunk at a position that is within at least one of the left and right lung. The denervation process, in some embodiments, is performed without permanently damaging other tissue structures. In some denervation procedures, substantially all of the nerve trunks extending along a tubular section of an airway are damaged to prevent substantially all nervous system signals transmitted along the airway from traveling past the denervated portion without destroying the airway.

In yet other embodiments, a method for denervating a bronchial tree of a subject includes moving an energy emitter of an instrument through the subject's skin. The energy emitter is positioned proximate to an airway. Nerve tissue of the bronchial tree is damaged using the energy emitter while the energy emitter is positioned outside of the airway. The energy emitter can output a sufficient amount of at least one of radiofrequency energy, microwave energy, radiation energy, high intensity focused ultrasound energy (HIFU), thermal energy, or combinations thereof to damage the nerve tissue. In radiofrequency ablation, the instrument may cool and protect nontargeted tissue. High intensity focused ultrasound energy can be delivered to specific targeted tissue to mitigate damage of nontargeted tissue. The instrument is removed from the subject, leaving the airway intact.

Non-invasive denervation methods can be used to denervate a subject's lungs. An external energy source can deliver energy to targeted tissue to form lesions. The lesions can be formed at a depth of 1 mm to 2 mm along an airway to insure that a nerve trunk is destroyed without destroying the entire airway wall.

A method in some embodiments comprises moving a distal section of an instrument through a subject's skin. Most of a bronchial tree is denervated using the instrument to substantially prevent nervous system signals from traveling to substantially all branches of the bronchial tree. The distal section can be percutaneously delivered to minimize trauma and reduce recovery time. The method can be performed without severing airways, removing airways, or otherwise damaging the entire circumference of the denervated airway. In some embodiments, the entire procedure is performed without severing the entire airway. The airway can continue to function after the procedure.

A denervation method includes moving an energy emitter of an instrument through the subject's skin. Nerve tissue is altered (e.g., damaged, ablated, etc.) using energy from the energy emitter while the energy emitter is positioned outside of an airway or organ. The instrument is removed from the subject without destroying the airway or organ. In certain embodiments, the airway remains intact through the entire denervation process such that the airway maintains the health of distal portions of the lung. The denervation method can be used to denervate one or both lungs.

In some embodiments, a distal section of an instrument is wrapped around an airway to position at least one energy emitter with respect to nerve tissue. The energy emitter can output energy to damage the nerve tissue. Visualization can be used to view the airway. In certain embodiments, the outside of the airway is visualized while performing an ablation procedure or positioning the energy emitter. Visualization can be achieved using at least one of a thoracoscope, an ultrasonic device, and a fluoroscopy system.

A wide range of different types of body structures can be treated using energy. Non-limiting exemplary body structures include airways, the trachea, esophagus, vessels (e.g., blood vessels), the urethra, or other targeted structures. In certain embodiments, an instrument is endovascularly positioned in a blood vessel to position a distal portion of the instrument proximate to an airway nerve or other target region. Energy is delivered from the instrument to damage the airway nerve such that nerve signals to the airway are attenuated.

In some embodiments, a method for denervating a bronchial tree or other body structure of a subject includes moving an energy emitter of an instrument through the subject's skin. Nerve tissue is damaged using energy from the energy emitter while the energy emitter is positioned outside of the airway or body structure. In certain procedures, the instrument is removed from the subject without severing the entire airway. The procedure can be performed without puncturing the wall of the airway or body structure.

In yet other embodiments, a method for treating a subject comprises delivering emitting energy from an external energy source positioned outside of the subject's body through the subject's skin towards targeted nerve tissue of a bronchial tree. The nerve tissue is damaged using the energy while the external energy source is outside the subject's body. The external energy source can be placed against or spaced apart from the subject's skin.

In further embodiments, a method comprises percutaneously delivering a distal section of an instrument through a subject's skin such that the distal section is positioned to damage nerve tissue of a bronchial tree, blood vessel, or other body structure. In bronchial tree procedures, at least a portion of a bronchial tree in a subject's lung is denervated using the instrument to substantially prevent nervous system signals from traveling to a portion of the bronchial tree. In vascular procedures, a catheter is endovascularly positioned a in a blood vessel to position a distal portion of the catheter proximate to an airway nerve. The catheter is used to ablate nerve tissue.

In certain embodiments, an instrument is endovascularly positioned in a blood vessel (e.g., a bronchial artery or other vessel) to position a distal portion of the instrument proximate to an airway structure, such as a nerve. Energy is delivered from the instrument to damage the airway nerve such that nerve signals to the airway are attenuated. Other tissues can also be targeted.

One or more electrodes carried by the distal portion of the catheter can output radiofrequency energy or ultrasound energy. The electrode can be coupled to an outside surface of the distal portion or positioned within the distal portion. By delivering the energy, nerve signals can be attenuated so as to reduce constriction of the airway. In some embodiments, the constriction is permanently eliminated. In yet other procedures, nerve signals are attenuated so as to inhibit constriction of smooth muscle in the airway.

In other procedures, an instrument is passed through a subject's mouth and into the esophagus. The distal section of the instrument can be manipulated to position the distal section of the instrument proximate to the bronchial tree. In certain embodiments, the distal section can push against the wall of the esophagus to position an ablation assembly proximate to the left main bronchus or the right main bronchus. Without puncturing the esophagus wall, the ablation assembly can deliver energy to the nerve tissue with or without employing differential cooling. The ablation assembly can remain within the lumen of the esophagus throughout the ablation process.

The instruments can be passed through openings in the esophagus, the trachea, the left main bronchus and/or the right main bronchus. To pass an instrument out of the trachea, an opening can be formed in the wall of the trachea. The instrument can be moved through the opening and proximate to nerve tissue of an airway. The nerve tissue can be ablated while the instrument extends through the trachea wall and alongside the airway. In other procedures, a puncture can be formed along the left and/or right main bronchus. The instrument can be delivered through the opening and can wrap around the bronchus to destroy or ablate tissue.

BRIEF DESCRIPTION OF THE SEVERAL VIEWS OF THE DRAWINGS

In the Figures, identical reference numbers identify similar elements or acts.

DETAILED DESCRIPTION

Figure 1:
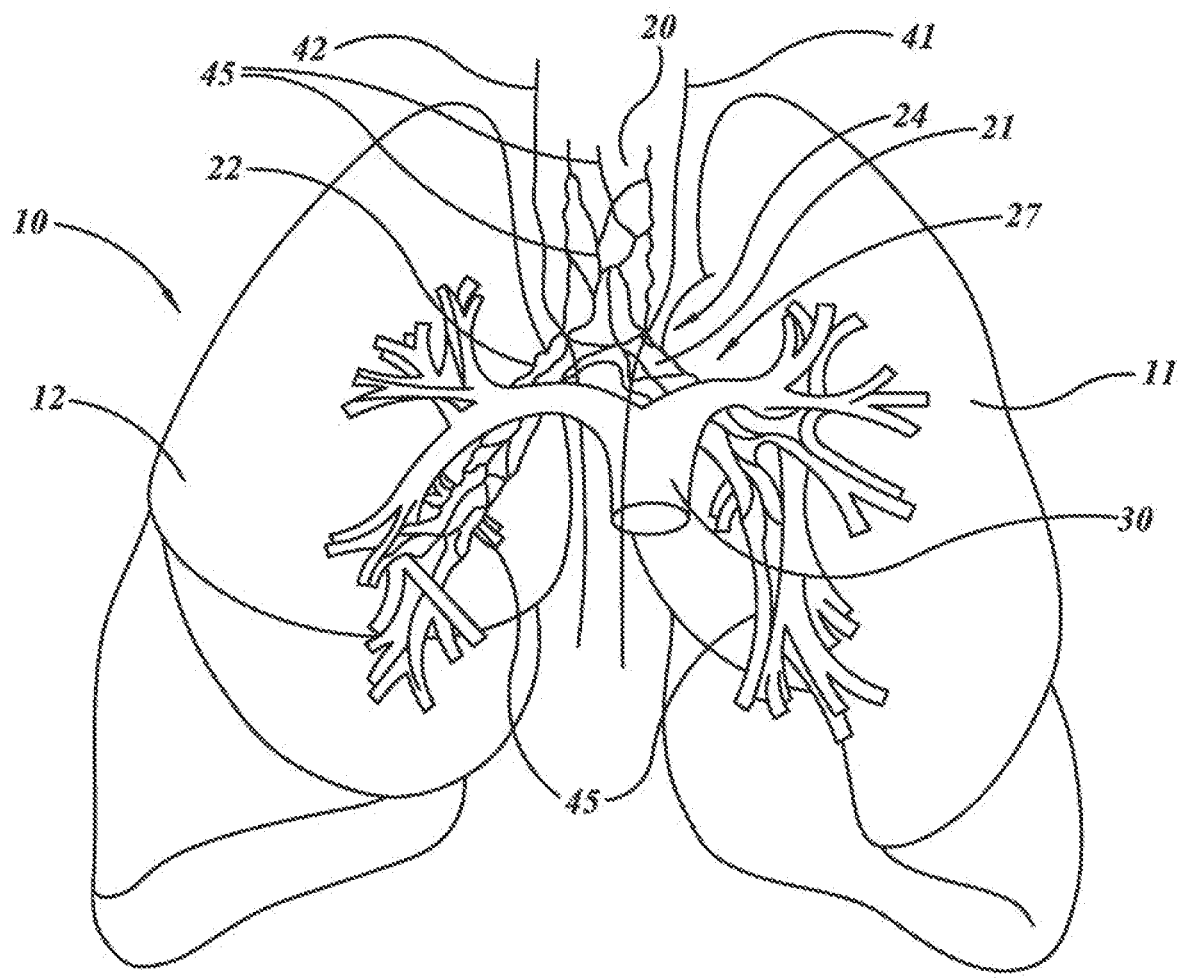
FIG. 1 is an illustration of lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen enriched blood then flows from the alveolar capillaries through the branching blood vessels of the pulmonary venous system to the heart. The heart pumps the oxygen rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways is largely parasympathetic in nature and travels between the lung and the brain in the right vagus nerve 42 and the left vagus nerve 41.

Figure 2:
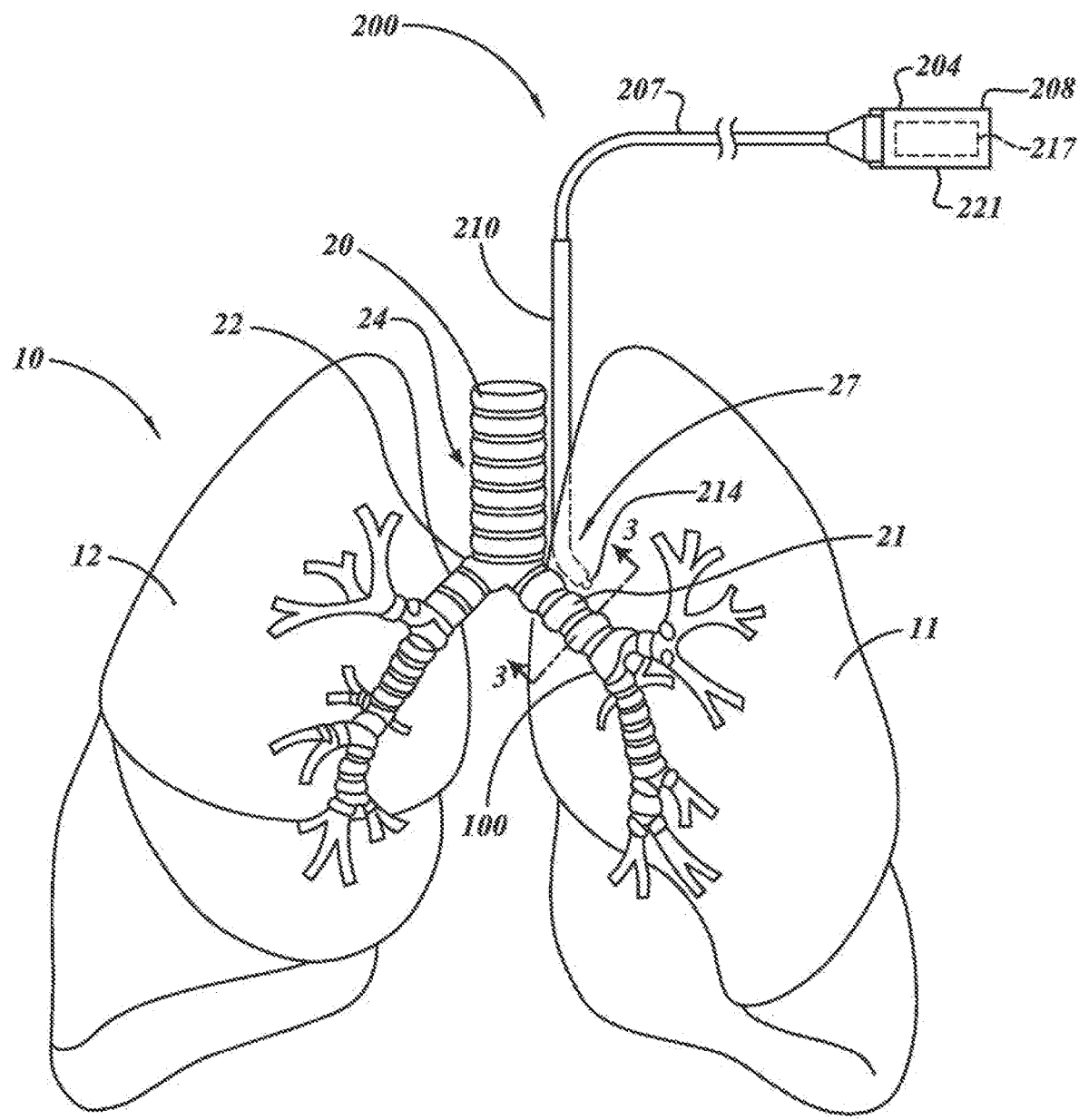
FIG. 2 is an illustration of a system positioned to treat a left main bronchus.

FIG. 2 shows a minimally invasive system 200 capable of treating the respiratory system to enhance lung function. The subject may suffer from COPD, asthma, or the like and, thus, the lungs 10 may perform poorly. To decrease air flow resistance to increase gas exchange, the system 200 can be used to perform a denervation procedure. A distal section 214 of an instrument 204 can affect nerve tissue, which can be part of a nerve trunk inside or outside of the lungs. The nerve tissue can be ablated to permanently dilate the airways and/or decrease airway mucus production or airway inflammation and edema.

The instrument 204 can be used to attenuate the transmission of signals traveling along the vagus nerves 41, 42 that cause or mediate muscle contractions, mucus 150 production, inflammation, edema, and the like. Attenuation can include, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs 10. Decreasing or stopping sensory input from the airways and lungs to local effector cells or to the central nervous system can also decrease reflex bronchoconstriction, reflex mucous production, release of inflammatory mediators, and nervous system input to other cells in the lungs or organs in the body that may cause airway wall edema. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. In some embodiments, the airway inflammation can be decreased a sufficient amount to cause a substantial decrease in airflow resistance and ongoing inflammatory injury to the airway wall. Signal attenuation may allow the smooth muscles to relax, prevent, limit, or substantially eliminate mucus production by mucous producing cells, and decrease inflammation. In this manner, healthy and/or diseased airways can be altered to adjust lung function. After treatment, various types of questionnaires or tests can be used to assess the subject's response to the treatment. If needed or desired, additional procedures can be performed to reduce the frequency of coughing, decrease breathlessness, decrease wheezing, and the like.

Main bronchi 21, 22 (i.e., airway generation 1) of FIGS. 1 and 2 can be treated to affect distal portions of the bronchial tree 27. In some embodiments, the left and right main bronchi 21, 22 are treated at locations along the left and right lung roots 24 and outside of the left and right lungs 11, 12. Treatment sites can be distal to where vagus nerve branches connect to the trachea and the main bronchi 21, 22 and proximal to the lungs 11, 12. A single treatment session involving two therapy applications can be used to treat most of or the entire bronchial tree 27. Substantially all of the bronchial branches extending into the lungs 11, 12 may be affected to provide a high level of therapeutic effectiveness. Because the bronchial arteries in the main bronchi 21, 22 have relatively large diameters and high heat sinking capacities, the bronchial arteries may be protected from unintended damage due to the treatment.

Nerve tissue distal to the main bronchi can also be treated, such as nerve tissue positioned outside the lung which run along the right or left main bronchi, the lobar bronchii, and bronchus intermedius. The intermediate bronchus is formed by a portion of the right main bronchus and includes origin of the middle and lower lobar bronchii. The distal section 214 can be positioned alongside higher generation airways (e.g., airway generations >2) to affect remote distal portions of the bronchial tree 27. Different procedures can be performed to denervate a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Each segmental bronchus may be treated by delivering energy to a single treatment site along each segmental bronchus. Nerve tissue of each segmental bronchus of the right lung can be destroyed. In some procedures, one to ten applications of energy can treat most of or substantially all of the right lung. Depending on the anatomical structure of the bronchial tree, segmental bronchi can often be denervated using one or two applications of energy.

Function of other tissue or anatomical features, such as the mucous glands, cilia, smooth muscle, body vessels (e.g., blood vessels), and the like can be maintained when nerve tissue is ablated. Nerve tissue includes nerve cells, nerve fibers, dendrites, and supporting tissue, such as neuroglia.

Nerve cells transmit electrical impulses, and nerve fibers are prolonged axons that conduct the impulses. The electrical impulses are converted to chemical signals to communicate with effector cells or other nerve cells. By way of example, a portion of an airway of the bronchial tree 27 can be denervated to attenuate one or more nervous system signals transmitted by nerve tissue. Denervating can include damaging all of the nerve tissue of a section of a nerve trunk along an airway to stop substantially all the signals from traveling through the damaged section of the nerve trunk to more distal locations along the bronchial tree or from the bronchial tree more proximally to the central nervous system. Additionally, signals that travel along nerve fibers that go directly from sensory receptors (e.g., cough and irritant receptors) in the airway to nearby effector cells (e.g., post-ganglionic nerve cells, smooth muscle cells, mucous cells, inflammatory cells, and vascular cells) will also be stopped. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation, mucous cells decrease mucous production, or inflammatory cells stop producing airway wall swelling and edema. These changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

Any number of procedures can be performed on one or more of these nerve trunks to affect the portion of the lung associated with those nerve trunks. Because some of the nerve tissue in the network of nerve trunks coalesces into other nerves (e.g., nerves connected to the esophagus, nerves though the chest and into the abdomen, and the like), specific sites can be treated to minimize, limit, or substantially eliminate unwanted damage of other nerves. Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways.

Figure 3:
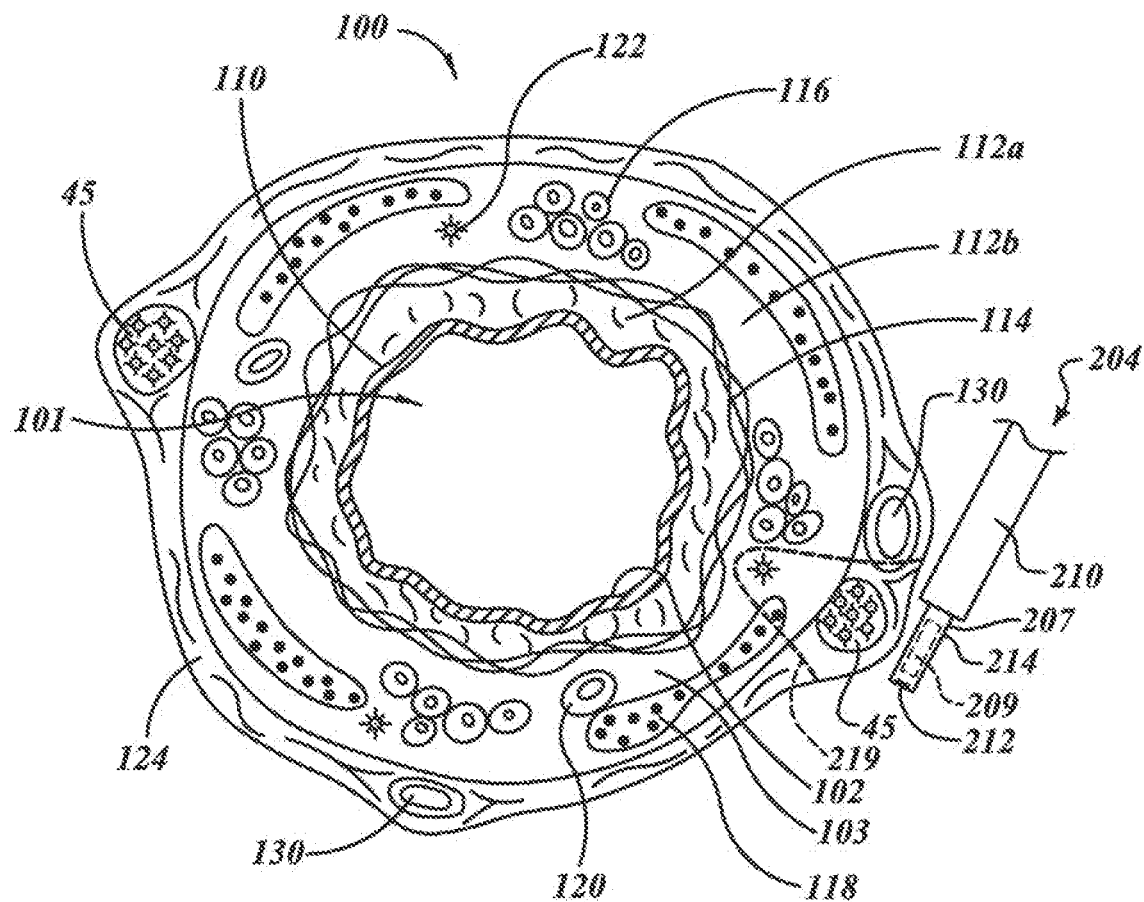
FIG. 3 is a cross-sectional view of an airway of a bronchial tree taken along a line 3-3 of FIG. 2.

Referring to FIGS. 2 and 3, the distal section 214 is positioned within the chest outside of the airway 100. An activatable element in the form of an energy emitter 209 (illustrated in dashed line) is configured to damage nerve tissue 45, illustrated as a vagus nerve branch. Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. There is a constant, baseline tonic activity of the efferent vagus nerve tissues to the airways which causes a baseline level of smooth muscle contraction and mucous secretion.

The energy emitter 209 can ablate the efferent and/or the afferent tissues to control airway smooth muscle (e.g., innervate smooth muscle), mucous secretion, nervous mediated inflammation, and tissue fluid content (e.g., edema). The contraction of airway smooth muscle, excess mucous secretion, inflammation, and airway wall edema associated with pulmonary diseases often results in relatively high air flow resistance causing reduced gas exchange and decreased lung performance.

The instrument 204 can be delivered through a percutaneous opening in the chest, back, or other suitable location. Potential access locations include between the ribs in the chest, between the ribs in a para-sternal location, between the ribs along the back or side of the subject, from a subxiphoid location in the chest, or through the pre-sternal notch superior to the manubrium. As used herein, the term "percutaneous" and derivations thereof refer generally to medical procedures that involve accessing internal organs via an opening, such as a puncture or small incision in a subject's skin and may involve the use of an access apparatus, such as the access apparatus 210. The access apparatus 210 can be in the form of a trocar, a cannula, a port, a sleeve, or other less-invasive access device, along with an endoscope, a thoracoscope, or other visualization device. The distal section 214 can be relatively sharp to puncture and pass through tissue. A stylet can be positioned in a lumen in the instrument 204 and can have a relatively sharp tip to directly puncture the skin. After the stylet is inserted into the skin, the instrument 204 can be moved along the stylet through the user's skin into and between internal organs.

The instrument 204 may be visualized using fluoroscopy, computed tomography (CT), thoracoscopy, ultrasound, or other imaging modalities, and may have one or more markers (e.g., radiopaque marks), or dyes (e.g., radiopaque dyes), or other visual features. The visual features can help increase the instrument's visibility, including the instrument's radiopacity or ultrasonic visibility.

An instrument shaft 207 of FIG. 2 can be made of a generally flexible material to allow delivery along tortuous paths to remote and deep sites. The distal section 214 can be steered or otherwise manipulated using a steering assembly 208. The distal section 214 can be deflected laterally or shaped into a desired configuration to allow enhanced navigation around thoracic structures. To deliver energy to a treatment site, the distal section 214 can assume a treatment configuration. The treatment configuration can be a serpentine configuration, a helical configuration, a spiral configuration, a straight configuration, or the like. U.S. patent application Ser. No. 12/463,304, filed on May 8, 2009, and U.S. patent application Ser. No. 12/913,702, filed on Oct. 27, 2010, describe catheters and apparatuses that can assume these types of configurations and can be used to perform the methods disclosed herein. Each of these applications is incorporated by reference in its entirety. Conventional electrode catheters or ablation catheters can also be used to perform at least some methods disclosed herein.

To damage nerve tissue 45, the distal section 214 can be at different orientations, including transverse to the nerve trunk 45, generally parallel to the nerve trunk 45, or any other suitable orientation with respect to the airway 100. If the tissue is ablated using chemicals, the distal section 214 can puncture the nerve trunk 45 and deliver the agent directly to nerve tissue.

As used herein, the term "energy" is broadly construed to include, without limitation, thermal energy, cryogenic energy (e.g., cooling energy), electrical energy, acoustic energy (e.g., ultrasonic energy), microwave energy, radiofrequency energy, high voltage energy, mechanical energy, ionizing radiation, optical energy (e.g., light energy), and combinations thereof, as well as other types of energy suitable for treating tissue. The energy emitter 209 of FIG. 3 can include one or more electrodes (e.g., needle electrodes, bipolar electrodes, or monopolar electrodes) for outputting energy, such as ultrasound energy, radiofrequency (RF) energy, radiation, or the like. The electrodes can output a sufficient amount of RF energy to form a lesion at the periphery of the airway 100. To avoid damaging smooth muscle tissue, a lesion 219 (shown in phantom line in FIG. 3) can have a depth less than or equal to about 2 mm. In some embodiments, the lesion depth D can be less than about 1 mm to localize tissue damage. Thermal energy emitters 209 can be resistive heaters or thermally conducting elements. To treat tissue with microwave energy, the energy emitter 209 can include one or more microwave antennas. In optical embodiments, the energy emitter 209 includes one or more lenses or reflector(s) capable of outputting light delivered via one or more optical fibers. An external light source (e.g., a lamp, an array of light emitting diodes, or the like) can output light that is delivered through the shaft 207 to the energy emitter 209. In other embodiments, the energy emitter 209 is a light source, such as a light-emitting diode (LED) or laser diode. Photodynamic agents or light activatable agents can be used to ablate tissue. In yet other embodiments, the energy emitter 209 can include a dispenser (e.g., a nozzle, an orifice, etc.) for delivering a substance (e.g., a chemical agent, a high temperature fluid, a cutting jet, etc.) that kills or damages targeted tissue. Multiple emitters can be used sequentially or simultaneously to treat tissue. For example, an energy emitter in the form of a dispenser can mechanically damage surface tissue while another energy emitter outputs radiofrequency or microwave energy to destroy deep tissue.

For mechanical denervation, the distal section 214 can mechanically damage tissue by cutting, abrading, or tearing nerve tissue. A minimal amount of tissue adjacent to the nerve tissue 45 may also be damaged. The damaged non-targeted tissue can heal without any appreciable decrease in lung function. In embodiments, the distal section 214 comprises a morcellation device.

The distal section 214 can comprise one or more energy absorption devices for absorbing energy from a remote energy source. The remote energy source can be a microwave energy source, a radiofrequency energy source, an ultrasound energy source, or a radiation energy source and can be positioned outside the subject's body or located in another body structure, such as the esophagus, airway (trachea or bronchus), or elsewhere in the subject's body. The distal section 214 can be heated by the remote energy source to a sufficient temperature to damage targeted tissue. Additionally or alternatively, the element 209 can include a reflector to reflect energy from a remote energy source. The reflected energy can create a pattern (e.g., interference pattern) to control the amplitude of energy waves at the target site.

With continued reference to FIG. 2, the controller 221 can include one or more processors, microprocessors, digital signal processors (DSPs), field programmable gate arrays (FPGA), and/or application-specific integrated circuits (ASICs), memory devices, buses, power sources, and the like. For example, the controller 221 can include a processor in communication with one or more memory devices. Buses can link an internal or external power supply to the processor. The memories may take a variety of forms, including, for example, one or more buffers, registers, random access memories (RAMs), and/or read only memories (ROMs). The controller 221 may also include a display, such as a screen, and can be a closed loop system, whereby the power to the distal section 214 is controlled based upon feedback signals from one or more sensors 212 (see FIG. 3) configured to transmit (or send) one or more signals indicative of one or more tissue characteristics, energy distribution, tissue temperature, or any other measurable parameters of interest. Based on those readings, the controller 221 can then adjust operation of the distal section 214. By way of example, the controller 221 can control the amount of energy delivered from the energy source 217 (e.g., one or more batteries or other energy storage devices) to the energy emitter 209. The sensor 212 can be a temperature sensor. If the temperature of the peripheral tissue of the airway 100 becomes too hot, the distal section 214 can cool the tissue using one or more Peltier devices, cooling balloons, or other types of cooling features. Current sensors or voltage sensors 212 can be used to measure the tissue impedance. Alternatively, the controller 221 can be an open loop system wherein the operation is set by user input. For example, the system 200 may be set to a fixed power mode. It is contemplated that the system 200 can be repeatedly switched between a closed loop mode and an open loop mode to treat different types of sites.

The instrument 204 can also include any number of different types of visualization devices, such as cameras, optical fibers, lenses, or mirrors. Ultrasound or other types of energy-based viewing systems can be used to visualize deep targeted tissues. Surface tissues can be targeted using direct visualization while deeper tissues are subsequently targeted using ultrasound.

Figure 4:
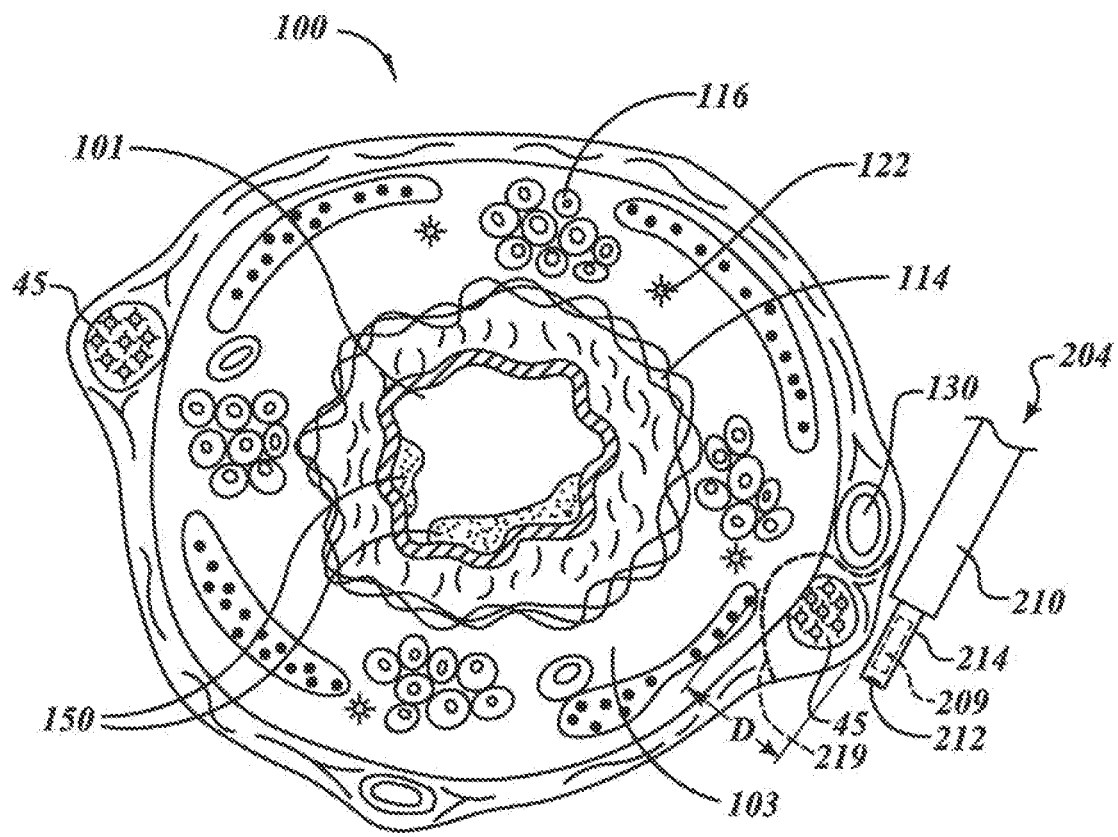
FIG. 4 is a cross-sectional view of a constricted airway and mucus is in an airway lumen and an instrument positioned next to the airway.

FIG. 4 shows a constricted, edematous and mucous filled airway 100 that can be dilated and can have mucous production and edema decreased by ablating the nerve tissue 45. As used herein, the term "ablate," including variations thereof, refers, without limitation, to destroying or permanently damaging, injuring, or traumatizing tissue. For example, ablation may include localized tissue destruction, cell lysis, cell size reduction, necrosis, or combinations thereof. In the context of pulmonary ablation applications, the term "ablation" includes sufficiently altering nerve tissue properties to substantially block transmission of electrical signals through the ablated nerve tissue. Ablating all of the nerve trunks along the airway prevents nerve signals from traveling distally along the airway 100 and causes the smooth muscle 114 to relax to open the airway 100.

In RF ablation, RF energy causes heating of the nerve tissue 45 and, ultimately, the formation of the lesion 219. The nerve tissue is destroyed without removing a significant amount of airway tissue, if any, to preserve the integrity of the airway 100. The lesion 219 can be left in the body to avoid potential complications from removing airway tissue. The healthy airway wall 103 prevents gas escape across the airway wall 103. The smooth muscle and interior lining of the airway 100 can remain substantially undamaged to allow mucociliary transport and other bodily functions that are important to overall health. This reduces the recovery time and avoids or mitigates problems associated with surgical techniques of removing or cutting through the airway wall. In contrast to lung resection procedures in which entire airways are severed and removed, an intact denervated airway 100 can also ensure that distal regions of the lung continue to function.

Large lesions can extend through the airway wall and can be formed to destroy unwanted tissue (e.g., cancerous tissues) positioned along the inner surface. Differential cooling can be used to form lesions buried deep within the sidewall 103, spaced apart from the interior and exterior surfaces of the airway 100, or any other suitable location. U.S. patent application Ser. No. 12/463,304, filed on May 8, 2009, and U.S. patent application Ser. No. 12/913,702, filed on Oct. 27, 2010 discloses various catheters and differential cooling techniques. The instrument 204 can cool tissues to keep the nontargeted tissue below a temperature at which cell death occurs. In some embodiments, the distal section 214 has a cooling member (e.g., a cooling balloon) that absorbs thermal energy to keep nontargeted regions of the airway wall 103 at or below a desired temperature. The shape and size of lesions can also be adjusted as desired.

Natural body functions can help prevent, reduce, or limit tissue damage. If the bronchial artery branch 130 is heated, blood within the blood vessels 130 can absorb the thermal energy and can then carry the thermal energy away from the heated section of the branches 130. The lesion 219 can surround a region of the blood vessel 130 without destroying the vessel 130. After the treatment is performed, the bronchial artery branches 130 can continue to maintain the health of lung tissue.

The lesion depth D of FIG. 4 can be kept at or below a desired depth by controlling the amount of delivered energy. To avoid reaching smooth muscle 114, the depth D can be equal to or less than about 3 mm, 2 mm, or 1 mm. For thick airway walls, the lesion depth D can be equal to or less than about 3 mm. For medium size airway walls, the lesion depth D can be equal to or less than about 2 mm. In young children with thin airway walls, the lesion depth D can be equal to or less than about 1 mm. The lateral dimensions (e.g., width, length, etc.) of the lesion 219 can be adjusted to ensure that targeted tissue is ablated.

Figure 5:
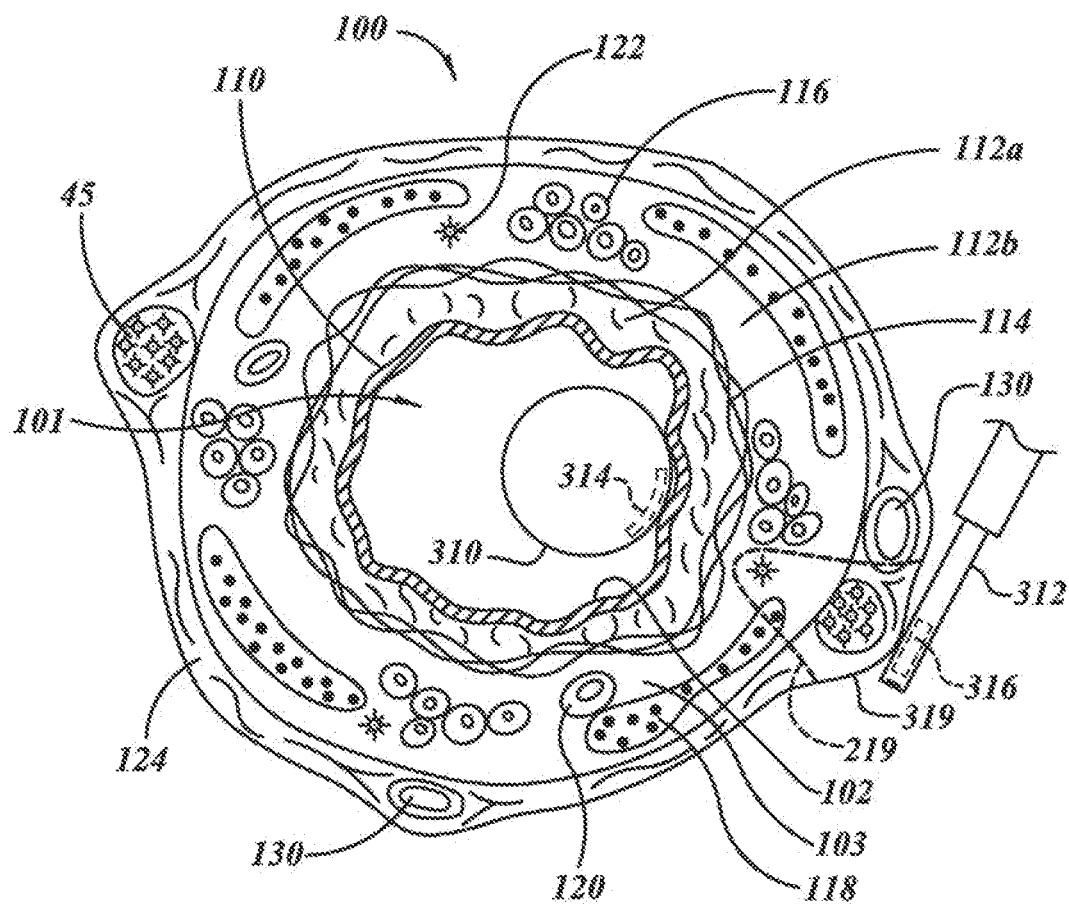
FIG. 5 is a cross-sectional view of an airway with an intraluminal instrument inside an airway and an instrument positioned outside the airway.

FIG. 5 shows a system that includes a pair of separately deliverable instruments 310, 312. The instrument 312 can be generally similar to the instrument 204 of FIGS. 2-4, unless indicated otherwise. The instrument 310 can be an intraluminal catheter deliverable through a lumen 101 defined by an inner surface 102 of the airway 100. The illustrated inner surface 102 is defined by a folded layer of epithelium 110 surrounded by stroma 112*a*. A layer of smooth muscle tissue 114 surrounds the stroma 112*a*. A layer of stroma 112*b* is between the muscle tissue 114 and connective tissue 124. Mucous glands 116, cartilage plates 118, blood vessels 120, and nerve fibers 122 are within the stroma layer 112*b*. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 via the nerve fibers 122.

The instrument 310 can be delivered along the trachea, esophagus, or other body structure in the vicinity of the treatment site. For example, the instrument 310 can extend through one or more organs to position an energy emitter 314 proximate to the targeted tissue. Instruments 310, 312 can cooperate to treat the targeted tissue therebetween. The instrument 310 can cool interior regions of the airway wall 103 to cause the formation of the lesion 219 at the outer periphery of the airway wall 103. For radiofrequency ablation, the RF energy can travel between bipolar electrodes 314, 316. Tissue impedance causes heating that can reach sufficiently high temperatures to cause cell death. To protect non-targeted tissues (e.g., interior tissue), the instrument 310 can cool the airway to keep the nontargeted tissue below a temperature at which cell death occurs.

Thermal energy can be absorbed by the instrument 312 to keep the exterior regions of the airway wall 103 at or below a desired temperature. Both instruments 310, 312 can provide cooling to form lesions generally midway through the airway wall 103. The amount of energy delivered and cooling capacity provided by the instruments 310, 312 can be adjusted to shape and form lesions at different locations.

At least one of the instruments 310, 312 can be adapted to tunnel through tissue or between adjacent structures to allow it to reach the desired location, for example, along the bronchi. Additionally or alternatively, the instruments 310, 312 may be adapted to adhere to or slide smoothly along tissue or to be urged against a structure (e.g., trachea, esophagus, and/or bronchi) as the instrument is advanced.

Figure 6:
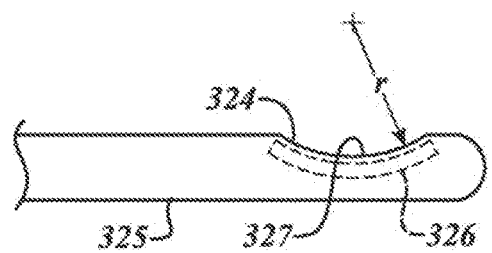
FIGS. 6-9 are side elevational views of distal sections of instruments.

FIG. 6 shows an instrument distal section 325 that includes a tissue-receiving region 324 and an energy emitter 326. The tissue-receiving region 324 has a concave surface 327 that generally matches a convex surface of an airway. A radius of curvature of the portion 324 can be approximately equal to the radius of curvature of the airway. When the distal section 325 is held against an airway, the energy emitter 326 can face targeted tissue.

Figure 6A:
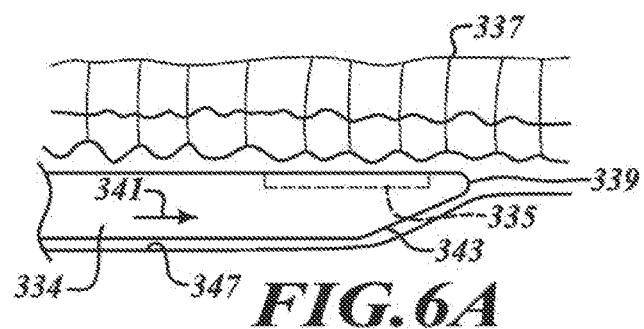

FIG. 6A shows an instrument distal section 334 that includes an energy emitter 335 facing an airway 337. A distal tip 339 is shaped to keep the energy emitter 335 facing the airway 337 as the distal section 334 is moved distally, as indicated by an arrow 341. For example, the slope region 343 can help separate tissue 347 to facilitate distal movement of the distal section 334.

Figure 7:
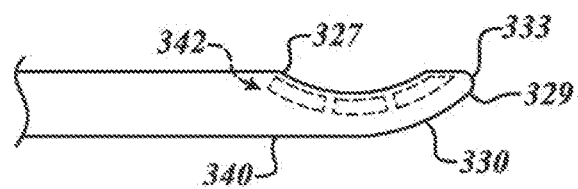

Referring to FIG. 7, an instrument distal section 330 includes a tissue-receiving surface 327 and an opposing guiding surface 329. The guiding surface 329 can slide smoothly along non-targeted tissue to facilitate advancement of the distal section 330. The curvature, contour, or slope of the guiding surface 329 can be selected to urge the tissue-receiving surface 327 against an anatomical structure. An energy emitter 342 (illustrated as a plurality of electrodes) can direct energy towards tissue received by the tissue-receiving surface 327. To position at least a portion of a nerve trunk in the surface 327, the tip 333 can be inserted between an airway and adjacent tissue.

Figure 8:
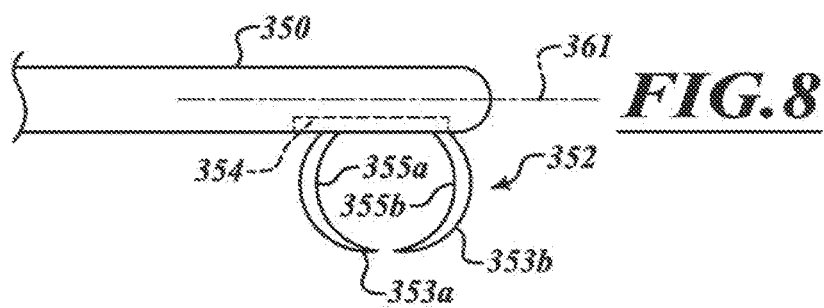
Figure 8A:
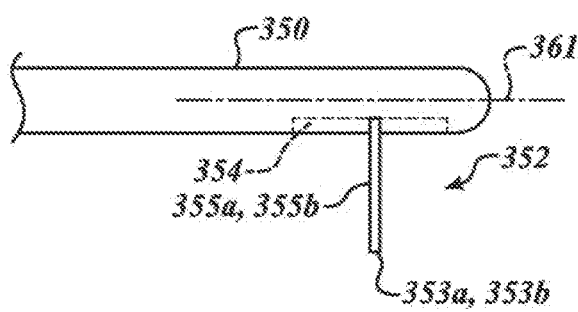
Figure 8B:
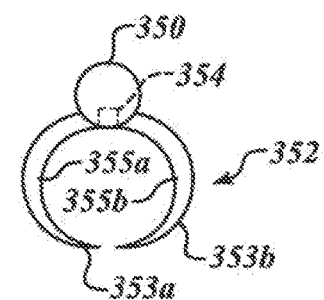

A wide range of different types of guides can partially or completely surround a structure, such as the esophagus, trachea, or bronchus. Guides may include, without limitation, a plurality of arms (e.g., a pair of arms, a set of curved or straight arms, or the like), a ring (e.g., a split ring or a continuous ring), or the like. FIGS. 8, 8A, and 8B show embodiments of an instrument distal section 350 with a guide 352 capable of surrounding a generally tubular structure. An emitter 354 is positioned to deliver energy to a structure held by the guide 352. The distal section 350 can be moved along the airway using the guide 352. The guide 352 can be pulled off the airway and used to slide the distal section 350 along another airway or other anatomical structure.

The illustrated guide 352 is a split ring lying in an imaginary plane that is generally perpendicular to a longitudinal axis 361 of the distal section 350. To treat the main bronchus, resilient arms 353a, 353b can be moved away from each other to receive the bronchus. The arms 353a, 353b can snuggly hold the bronchus to allow atraumatic sliding. Surface 355a, 355b can slide smoothly along an airway or other body structure. In some embodiments, the guide 352 is pivotally coupled to the instrument shaft to allow the guide 352 to rotate as it moves along a structure.

Figure 9:
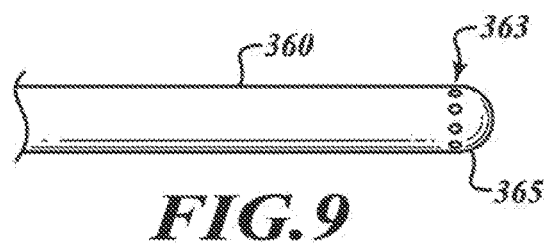

FIG. 9 shows an instrument distal section 360 with guides in the form of openings 363. The openings 363 are circumferentially spaced about the periphery of a main body 365. A vacuum can be drawn through one or more of the openings 363 to hold the distal section 360 against tissue. In other embodiments, fluids can be delivered out of one or more of the openings 363 to push the distal section 360 in a desired direction.

Figure 10:
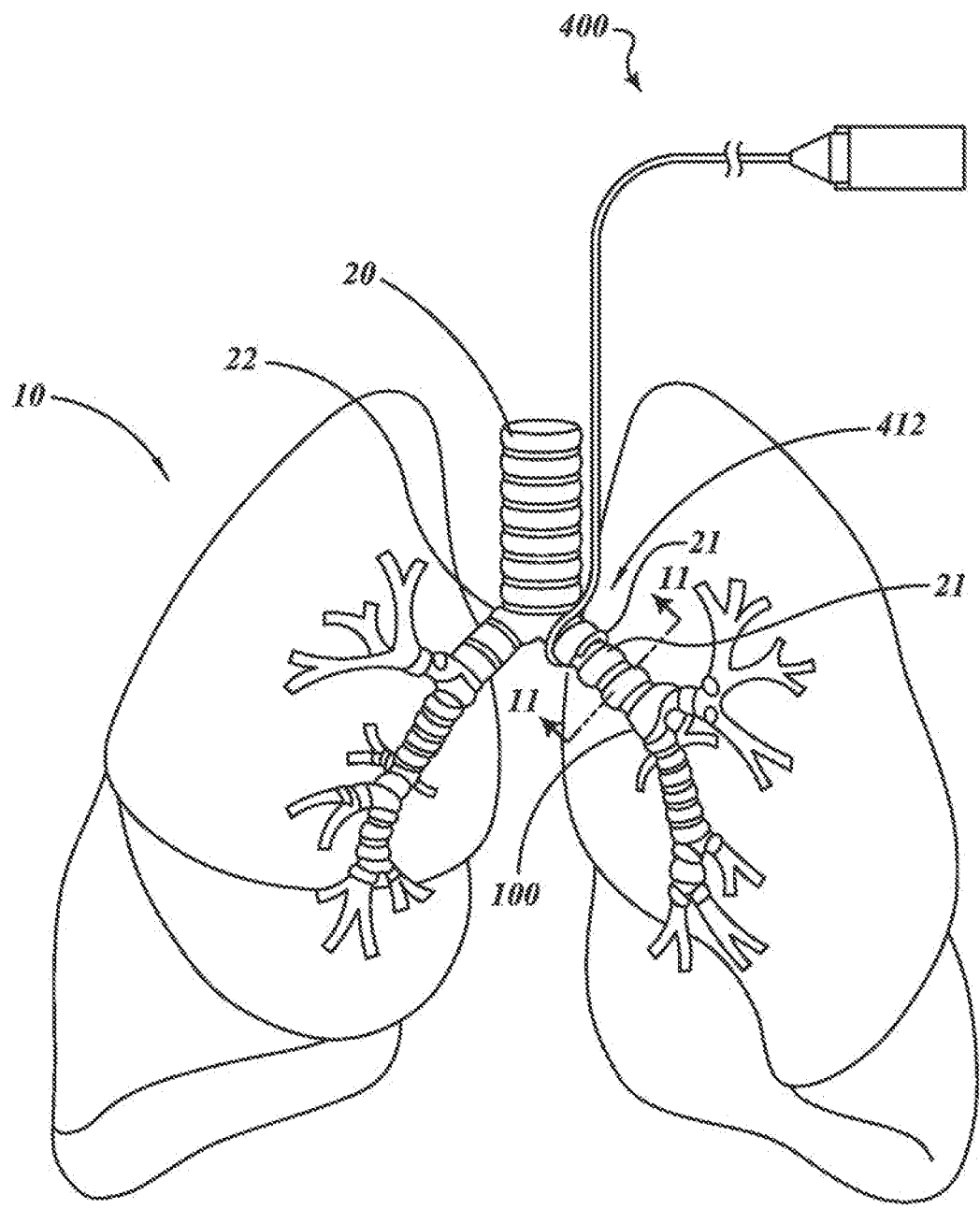
FIG. 10 is an illustration of an instrument surrounding a left main bronchus.
Figure 11:
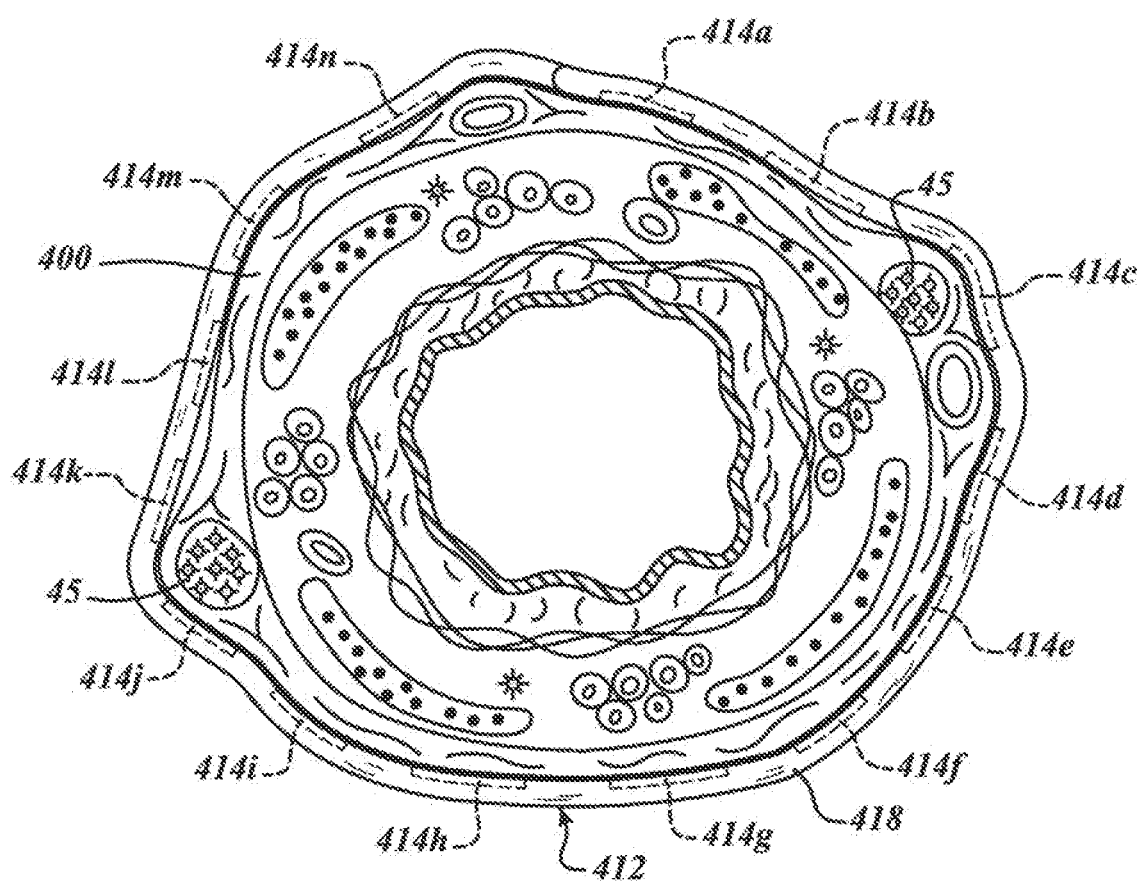
FIG. 11 is a cross-sectional view of the left main bronchus of taken along a line 11-11 of FIG. 10.

FIG. 10 shows an instrument 400 with a distal section 412 wrapped around a left main bronchus. The distal section 412 can be configured to assume a helical shape or spiral shape. As shown in FIG. 11, energy emitters 414a-414n (collectively "414") can deliver energy directly to the airway 100. An outer region 418 of the distal section 412 may not output energy to protect adjacent tissue. As such, the distal section 412 can effectively emit energy towards the airway 100. In other embodiments, the distal section 412 can output energy in all directions. A protective sleeve can be positioned over the applied distal section 412 to protect adjacent tissue. The sleeve can be made of an insulating material.

To treat the nerves 45, the electrodes 414c, 414j, 414k can be activated. The other electrodes 414 can remain inactive. In other embodiments, a continuous electrode can extend along the length of the distal section 414. The continuous electrode can be used to form a helical or spiral shaped lesion. In certain embodiments, the continuous electrode can have addressable sections to allow for selective ablation.

Airway cartilage rings or cartilage layers typically have a significantly larger electrical resistance than airway soft tissue (e.g., smooth muscle or connective tissue). Airway cartilage can impede the energy flow (e.g., electrical radiofrequency current flow) and makes the formation of therapeutic lesions to affect airway trunks challenging when the electrode is next to cartilage. The electrodes 414 can be positioned to avoid energy flow through cartilage. For example, the electrode 414 can be positioned between cartilage rings. Most or substantially all of the outputted energy can be delivered between the rings in some procedures. Tissue impedance can be measured to determine whether a particular electrode is positioned next to a cartilage ring, in an intercartilaginous space, or at another location.

Referring again to FIG. 10, the instrument 400 may have a lumen to receive a stylet to straighten and stiffen the preshaped distal section 412 during introduction. After insertion, the stylet can be withdrawn to allow the preshaped distal section 412 to assume a treatment configuration (e.g., a spiral configuration, a helical configuration, or the like). Alternatively, the distal section 412 may be relatively flexible and straight during introduction. A stylet having a shape corresponding to a desired shape may be inserted into the instrument 400 to impart the desired shape to the distal section 412. In a further embodiment, the instrument 400 may be shapeable or steerable using an actuator at its proximal end to allow it to be steered so as to surround the target tubular structure. Various steering mechanisms can be used, including, for example, one or more pull wires anchored to a distal tip at a point offset from the center line. The wire(s) can extend slidably through one or more lumens in the instrument 400 to the proximal end where they may be tensioned by an actuator so as to deflect the distal section 412.

Figure 12:
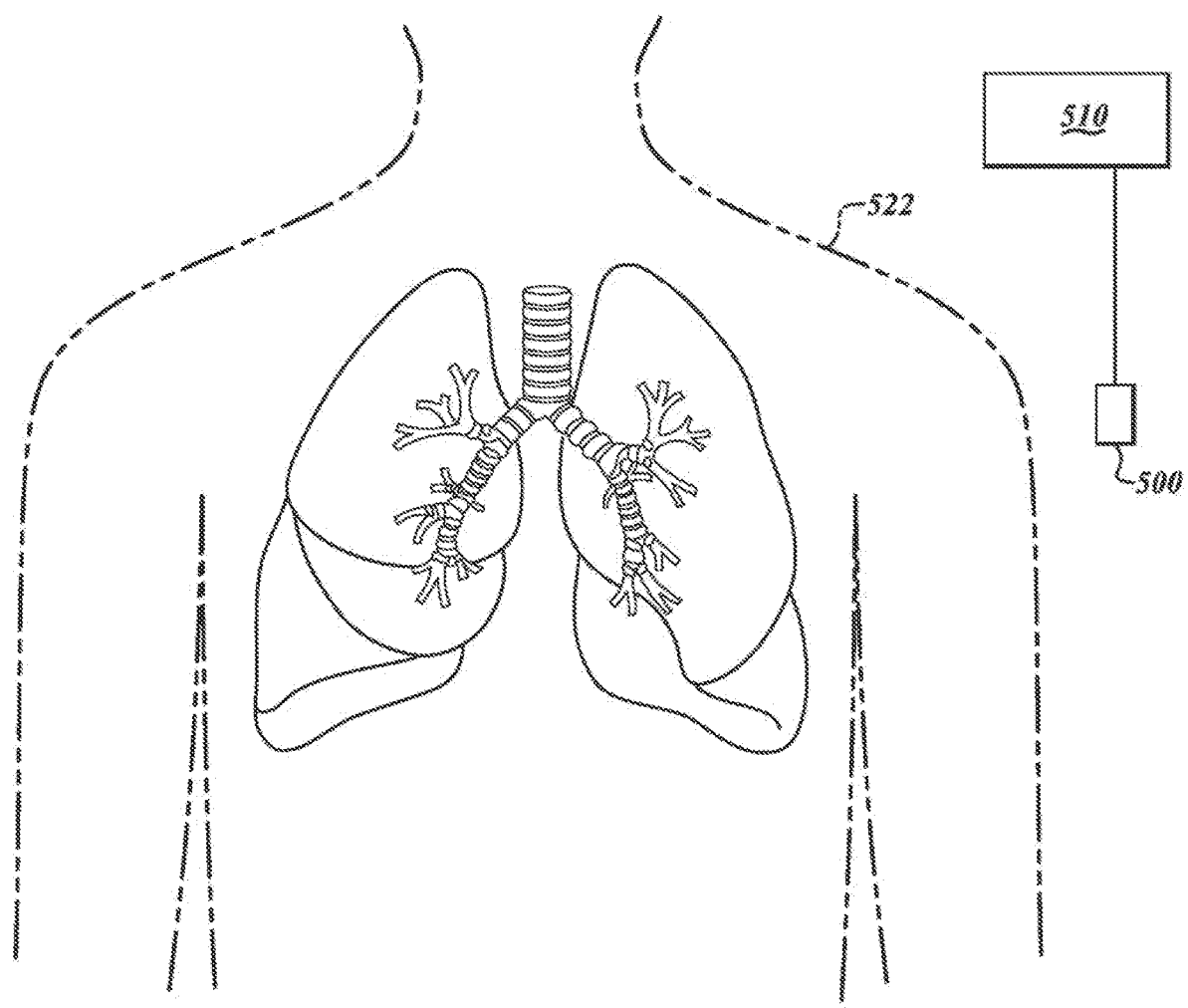
FIG. 12 is an illustration of an external treatment system and a subject.

FIG. 12 shows a system for non-invasively denervating a bronchial tree. An external energy source 500 is connected to an energy delivery system 510. The external energy source 500 can emit a beam of radiation to targeted tissue, such as nerve tissue. The beam of radiation can destroy the targeted tissue. The system can include, or be in the form of, a CyberKnife® Robotic Radiosurgery System from Accuray®, a TomoTherapy® radiation therapy system, or similar type of systems capable of targeting moving tissue, thereby mitigating or limiting damage to non-targeted tissue.

Beam radiation may be delivered from different remote locations to damage deep nerve tissue without damaging intervening tissues. The source of beam radiation may be a beam emitter 500 of an external beam radiotherapy system or a stereotactic radiation system 510. Because the lungs and bronchi move as the subject breathes, the system can be adapted to target moving tissues. By positioning the radiation beam emitter 500 at various locations relative to the patient's body 522, such systems may be used to deliver a radiation beam from various angles to the targeted nerve tissue. The dose of radiation given to intervening tissues may be insufficient to cause injury, but the total dose given to the target nerve tissue is high enough to damage (e.g., ablate) the targeted tissue.

Ultrasound can be used to damage targeted tissue. High intensity focused ultrasound may be used to target and damage the nerve tissue. The external energy source 500 can be a HIFU emission device. Alternatively, a catheter, an intra-luminal instrument, or other type of instrument for insertion into the body can include a HIFU emission device. By way of example, the element 209 of FIG. 3 can be a HIFU emission device. Such embodiments are well suited for delivery through another body structure, such as the esophagus or airway, to treat target tissue of an airway. The HIFU instrument may include ultrasound imaging capability to locate the targeted tissues. The HIFU instrument can emit a plurality of ultrasound "beams" from different angles toward the target tissues. The intensity of any one of the beams can be insufficient to damage intervening tissues. The beams can interfere at the target site and together have sufficient magnitude to damage the target nerve tissue.

The HIFU-based systems can be adapted to target moving tissues. For example, such systems may have a computer-controlled positioning system which receives input from an ultrasound or other imaging system and commands a positioning system in real time to maintain the HIFU device in a fixed position relative to the target structure.

Instruments disclosed herein may be entirely or partially controlled robotically or by a computer. Instruments may be attachable to a computer-controlled robotic manipulator which moves and steers the instruments. Robotic systems, such as the da Vinci® Surgical System from Intuitive Surgical or the Sensei Robotic Catheter system from Hansen Medical, Inc., or similar types of robotic systems, can be used. The instruments can have a proximal connector (e.g., an adaptor mechanism) that connects with a complementary fitting on the robotic system and links movable mechanisms of the instrument with control mechanisms in the robotic system. The instrument connector can also provide electrical couplings for wires leading to energy emitters, electrodes, microwave antennae, or other electrically powered devices. The instrument may further include sensor devices (e.g., temperature sensors, tissue impedance sensors, etc.) which are also coupled via the connector of the robotic system. The robotic system can include a control module that allows the physician to move and activate the denervation instrument while visualizing the location of the instrument within the chest, for example, using thoracoscopy, fluoroscopy, ultrasound, or other suitable visualization technology. The instrument may also be computer controlled, with or without robotic manipulation. A computer may receive feedback (e.g., sensory data) from sensors carried by the instrument or elsewhere to control positioning, power delivery, or other parameters of interest. For example, in energy-based denervation embodiments, a computer may be used to receive temperature data from temperature sensors of the instrument and to control power delivery to avoid overheating of tissue.

The instruments can access sites through blood vessels, as well as external to the organs. Robot surgery (including robotic catheter systems), natural orifice access methods, and minimally invasive access methods such as using trocar access methods and thoracoscopy have provided clinicians with access procedure locations within the human body and also minimized patient morbidity and complications due to surgery.

The assemblies, methods, and systems described herein can be used to affect tissue which is located on the outside of hollow organs, such as the lung, esophagus, nasal cavity, sinus, colon, vascular vessels and the like or other solid organs. Various types of activatable elements (e.g., energy emitters) can be utilized to output the energy. The activatable elements can be sufficiently small to facilitate percutaneous delivery to minimize or limit trauma to the patient.

The embodiments disclosed herein can treat the digestive system, nervous system, vascular system, or other systems. The treatment systems and its components disclosed herein can be used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue, the bronchial tree, or the like. Access techniques and procedures used to provide access to a target region can be performed by a surgeon and/or a robotic system. Those skilled in the art recognize that there are many different ways that a target region can be accessed. The various embodiments h such claims are entitled. Accordingly, the claims are not limited by the disclosure. described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method to denervate at least a portion of a bronchial tree, the method comprising:
   providing an instrument to a user, the instrument including an energy emitter positioned at a distal section of the instrument; and
   providing instructions to the user, the instructions comprising:
      moving the energy emitter through a skin of a subject;
      wrapping the distal section of the instrument around an airway of the bronchial tree of the subject to position the energy emitter with respect to nerve tissue along the airway of the bronchial tree;
      energizing the energy emitter to damage the nerve tissue using energy from the energy emitter while the energy emitter is positioned outside of the airway; and
      removing the instrument from the subject.

2. The method of claim 1, wherein providing instructions to the user comprises providing instructions for use or directions for accessing instructions for use, the instructions for use or directions being recorded on a tangible medium.

3. The method of claim 1, wherein the instructions further comprise monitoring the airway so as to leave the airway intact.

4. The method of claim 1, wherein the instructions for energizing the energy emitter to damage the nerve tissue further comprise instructions for ablating a section of a nerve trunk to impede transmission of nervous system signals traveling along the airway.

5. The method of claim 1, wherein the instructions for energizing the energy emitter to damage the nerve tissue further comprise delivering at least one of radiofrequency energy, microwave energy, radiation energy, high intensity focused ultrasound energy, and thermal energy from the energy emitter to damage the nerve tissue.

6. The method of claim 1, wherein wrapping the distal section of the instrument around an airway of the bronchial tree of the subject to position the energy emitter with respect to nerve tissue along the airway of the bronchial tree further comprises delivering the energy emitter proximate to the nerve tissue prior to damaging the nerve tissue.

7. The method of claim 1, wherein the instructions further comprise:
   moving an intraluminal instrument through the subject's trachea and the airway; and
   delivering energy between the energy emitter of the instrument outside the airway and the intraluminal instrument positioned within the airway to ablate the nerve tissue.

8. The method of claim 1, wherein the instructions for energizing the energy emitter to damage the nerve tissue further comprise instructions for irreversibly damaging nerve tissue between the subject's trachea and the subject's lung to at least partially block a transmission of nervous system signals and to cause a permanent decrease in smooth muscle tone of the portion of a bronchial tree.

9. The method of claim 1, wherein the instructions for energizing the energy emitter to damage the nerve tissue the nerve tissue further comprise instructions for ablating the nerve tissue while monitoring the airway so as not to pass the instrument through a wall of the airway.

10. The method of claim 1, wherein the instructions for energizing the energy emitter to damage the nerve tissue further comprise instructions for destroying the nerve tissue while monitoring the airway so as not to substantially damage blood vessels of the airway.

11. The method of claim 1, wherein the instructions for energizing the energy emitter to damage nerve tissue further comprise instructions for damaging nerve tissue positioned along a main bronchus of the bronchial tree.

12. The method of claim 1, wherein the instructions further comprise visualizing the outside of the airway while positioning the energy emitter using a visualization device selected from a group consisting of a thoracoscope, an ultrasonic device, and a fluoroscopy system.

13. The method of claim 1, wherein the instructions for moving the energy emitter through the skin of a subject further comprise moving the energy emitter through a port, a cannula, or a sleeve extending through the skin of the subject.

14. A method to denervate at least a portion of a bronchial tree, the method comprising:
    providing an instrument to a user; and
    providing instructions to the user, the instructions comprising:
        percutaneously delivering a distal section of the instrument through a skin of a subject and wrapping the distal section of the instrument around an airway of a bronchial tree of the subject such that the distal section is positioned to damage nerve tissue of the bronchial tree; and
        delivering energy to a first portion of the bronchial tree using the instrument to substantially inhibit nervous system signals from traveling to a second portion of the bronchial tree.

15. The method of claim 14, wherein providing instructions to the user comprises providing instructions for use or directions for accessing instructions for use, the instructions for use or directions being recorded on a tangible medium.

16. The method of claim 14, wherein the instructions further comprise damaging a nerve trunk positioned along a main bronchus.

17. The method of claim 14, wherein the instructions for denervating the first portion of the bronchial tree further comprise instructions for damaging nerve tissue positioned between the subject's trachea and lung.

18. The method of claim 14, wherein the instructions for denervating the first portion of the bronchial tree further comprise instructions for ablating a sufficient amount of nerve tissue to prevent nervous system signals from traveling to substantially all bronchial branches of the bronchial tree.

19. The method of claim 14, wherein the instructions for denervating the first portion of the bronchial tree further comprise instructions for removing the instrument without destroying the airway.

20. The method of claim 14, wherein the instructions for percutaneously delivering a distal section of the instrument through the skin of a subject further comprise instructions for delivering a distal section of the instrument through a port, a cannula, or a sleeve extending through the subject's skin.

\* \* \* \* \*